(12) United States Patent
Petursson

(10) Patent No.: US 11,253,384 B2
(45) Date of Patent: Feb. 22, 2022

(54) ORTHOPEDIC DEVICE, STRAP SYSTEM AND METHOD FOR SECURING THE SAME

(71) Applicant: Ossur Iceland ehf, Reykjavik (IS)

(72) Inventor: Valgeir Petursson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 658 days.

(21) Appl. No.: 15/614,863

(22) Filed: Jun. 6, 2017

(65) Prior Publication Data

US 2017/0348130 A1 Dec. 7, 2017

Related U.S. Application Data

(60) Provisional application No. 62/434,862, filed on Dec. 15, 2016, provisional application No. 62/346,190, filed on Jun. 6, 2016.

(51) Int. Cl.
*A61F 5/01* (2006.01)
*A44B 11/25* (2006.01)
(Continued)

(52) U.S. Cl.
CPC .......... *A61F 5/0123* (2013.01); *A61F 5/0102* (2013.01); *A61F 5/0109* (2013.01);
(Continued)

(58) Field of Classification Search
CPC .......... Y10T 24/45058; Y10T 24/45063; Y10T 24/45225; Y10T 24/4523; A44B 11/00; A44B 11/006; A44B 11/0258; A44B 11/20; A44B 11/25; A44B 11/2553; A44B 11/2557; A44B 11/2584; A44B 11/28; A61F 5/0102; A61F 5/0104; A61F 5/0106; A61F 5/0123; A61F 5/01; A61F 5/0109; A61F 2005/0132; A61F 2005/0146;
(Continued)

(56) References Cited

U.S. PATENT DOCUMENTS 667,768 A 2/1901 Puy
777,585 A 12/1904 Beatty
(Continued)

FOREIGN PATENT DOCUMENTS

CN 101128169 A 2/2008
DE 846 895 C 8/1952
(Continued)

OTHER PUBLICATIONS

Article: "An Orthosis for Medial or Lateral Stabilization of Arthritic Knees", by S. Cousins and James Foort, Orthotics and Prosthetics, vol. 29, No. 4, pp. 21-26, Dec. 1975.
(Continued)

*Primary Examiner* — Keri J Nelson
(74) *Attorney, Agent, or Firm* — Workman Nydegger

(57) ABSTRACT

An orthopedic device includes a frame, a strap system including first and second straps connecting to the frame, and an adjustment mechanism couples to the first and second straps and simultaneously regulates tension in the first and second straps by moving the first and second straps relative to the frame. The strap system includes a length adjustment system for modifying the length of the strap.

19 Claims, 10 Drawing Sheets

(51) Int. Cl.
*A44B 11/28* (2006.01)
*A44B 13/00* (2006.01)

(52) U.S. Cl.
CPC ............ *A44B 11/258* (2013.01); *A44B 11/28* (2013.01); *A44B 13/0029* (2013.01); *A61F 5/01* (2013.01); *A61F 2005/0132* (2013.01); *A61F 2005/0137* (2013.01); *A61F 2005/0146* (2013.01); *A61F 2005/0158* (2013.01); *A61F 2005/0167* (2013.01); *A61F 2005/0174* (2013.01); *A61F 2005/0181* (2013.01); *A61F 2250/0004* (2013.01)

(58) Field of Classification Search
CPC ...... A61F 2005/0158; A61F 2005/0174; A61F 2005/0181
USPC ...... 128/876; 602/75, 78, 79, 23, 26, 60–62; 2/304, 325, 309, 311; 24/578.1, 578.14, 24/578.15, 591.1, 592.1
See application file for complete search history.

(56) References Cited

U.S. PATENT DOCUMENTS

| | | |
|---|---|---|
| 937,478 A | 10/1909 | Sims |
| 1,153,334 A | 9/1915 | Oswald |
| 1,227,700 A | 5/1917 | Tucker |
| 1,328,541 A | 1/1920 | Palmer |
| 1,510,408 A | 9/1924 | Lychou |
| 1,593,631 A | 7/1926 | Harsh |
| 1,622,211 A | 3/1927 | Sheehan |
| 1,825,898 A | 10/1931 | Coulter |
| 2,032,923 A | 3/1936 | Eldridge |
| 2,179,903 A | 11/1939 | Spears |
| 2,467,907 A | 4/1949 | Peckham |
| 2,573,866 A | 11/1951 | Murphy |
| 2,717,841 A | 9/1955 | Biefeld et al. |
| 2,935,065 A | 5/1960 | Homier et al. |
| 3,031,730 A | 5/1962 | Morin |
| 3,046,981 A | 7/1962 | Biggs, Jr. et al. |
| 3,089,486 A | 5/1963 | Pike |
| 3,266,113 A | 8/1966 | Flanagan, Jr. |
| 3,463,147 A | 8/1969 | Stubbs |
| 3,514,313 A | 5/1970 | Martel et al. |
| 3,520,765 A | 7/1970 | Bateman |
| 3,528,412 A | 9/1970 | McDavid |
| 3,581,741 A | 1/1971 | Rosman |
| 3,561,436 A | 2/1971 | Gaylord, Jr. |
| 3,594,863 A | 7/1971 | Erb |
| 3,594,865 A | 7/1971 | Erb |
| 3,742,557 A | 7/1973 | Francois |
| 3,752,619 A | 8/1973 | Menzin et al. |
| 3,758,657 A | 9/1973 | Menzin et al. |
| 3,789,842 A | 2/1974 | Froimson |
| 3,804,084 A | 4/1974 | Lehman |
| 3,817,244 A | 6/1974 | Taylor |
| 3,851,357 A | 12/1974 | Ribich et al. |
| 3,877,426 A | 4/1975 | Nirschl |
| 3,916,077 A | 10/1975 | Damrau |
| 3,927,881 A | 12/1975 | Lemelson et al. |
| 3,945,046 A | 3/1976 | Stromgren |
| 3,955,565 A | 5/1976 | Johnson, Jr. |
| 4,130,115 A | 12/1978 | Taylor |
| 4,193,395 A | 3/1980 | Gruber |
| 4,204,532 A | 5/1980 | Lind et al. |
| 4,240,414 A | 12/1980 | Theisler |
| 4,269,179 A | 5/1981 | Burton et al. |
| 4,269,181 A | 5/1981 | Delannoy |
| 4,275,716 A | 6/1981 | Scott, Jr. |
| 4,280,489 A | 7/1981 | Johnson, Jr. |
| 4,291,072 A | 9/1981 | Barrett et al. |
| 4,296,744 A | 10/1981 | Palumbo |
| 4,304,560 A | 12/1981 | Greenwood |
| 4,312,335 A | 1/1982 | Daniell, Jr. |
| 4,336,279 A | 6/1982 | Metzger |
| 4,372,298 A | 2/1983 | Lerman |
| 4,381,768 A | 5/1983 | Erichsen et al. |
| 4,381,769 A | 5/1983 | Prahl |
| 4,386,723 A | 6/1983 | Mule |
| 4,396,012 A | 8/1983 | Cobiski |
| 4,470,857 A | 9/1984 | Casalou |
| 4,472,461 A | 9/1984 | Johnson |
| 4,506,661 A | 3/1985 | Foster |
| 4,528,440 A | 7/1985 | Ishihara |
| 4,554,913 A | 11/1985 | Womack et al. |
| 4,556,053 A | 12/1985 | Irons |
| 4,572,170 A | 2/1986 | Cronk et al. |
| 4,617,214 A | 10/1986 | Billarant |
| 4,632,098 A | 12/1986 | Grundei et al. |
| 4,677,713 A | 7/1987 | Copp |
| 4,693,921 A | 9/1987 | Billarant et al. |
| D292,529 S | 10/1987 | Saare |
| 4,697,583 A | 10/1987 | Mason et al. |
| 4,724,831 A | 2/1988 | Huntjens |
| 4,768,500 A | 9/1988 | Mason et al. |
| 4,775,310 A | 10/1988 | Fischer |
| D298,568 S | 11/1988 | Womack et al. |
| 4,782,605 A | 11/1988 | Cahpnick |
| 4,791,916 A | 12/1988 | Paez |
| 4,794,028 A | 12/1988 | Fischer |
| 4,801,138 A | 1/1989 | Airy et al. |
| 4,802,939 A | 2/1989 | Billarant et al. |
| 4,805,606 A | 2/1989 | McDavid, III |
| 4,854,308 A | 8/1989 | Drillio |
| 4,856,501 A | 8/1989 | Castillo et al. |
| 4,856,502 A | 8/1989 | Ersfeld et al. |
| 4,872,243 A | 10/1989 | Fischer |
| 4,922,929 A | 5/1990 | DeJournett |
| 4,933,035 A | 6/1990 | Billarant et al. |
| 4,953,543 A | 9/1990 | Grim et al. |
| 4,961,544 A | 10/1990 | Bidoia |
| 4,966,133 A | 10/1990 | Kausek |
| 4,989,593 A | 2/1991 | Campagna et al. |
| 4,991,574 A | 2/1991 | Pocknell |
| 4,991,640 A | 2/1991 | Verkindt et al. |
| 5,002,045 A | 3/1991 | Spademan |
| 5,005,627 A | 4/1991 | Hatfield |
| 5,016,621 A | 5/1991 | Bender |
| 5,018,514 A | 5/1991 | Grood et al. |
| 5,020,196 A | 6/1991 | Panach et al. |
| 5,022,109 A | 6/1991 | Pekar |
| 5,063,916 A | 11/1991 | France et al. |
| 5,067,772 A | 11/1991 | Koa |
| 5,077,870 A | 1/1992 | Melbye et al. |
| 5,085,210 A | 2/1992 | Smith, III |
| 5,112,296 A | 5/1992 | Beard et al. |
| 5,152,038 A | 10/1992 | Schoch |
| 5,154,682 A | 10/1992 | Kellerman |
| 5,157,813 A | 10/1992 | Carroll |
| 5,181,331 A | 1/1993 | Berger |
| 5,227,698 A | 7/1993 | Simpson et al. |
| 5,242,379 A | 9/1993 | Harris et al. |
| 5,267,951 A | 12/1993 | Ishii |
| 5,277,697 A | 1/1994 | France et al. |
| 5,277,698 A | 1/1994 | Taylor |
| 5,288,287 A | 2/1994 | Castillo et al. |
| 5,302,169 A | 4/1994 | Taylor |
| 5,306,230 A | 4/1994 | Bodine |
| 5,314,455 A | 5/1994 | Johnson, Jr. et al. |
| 5,316,547 A | 5/1994 | Gildersleeve |
| 5,322,729 A | 6/1994 | Heeter et al. |
| 5,334,135 A | 8/1994 | Grim et al. |
| 5,344,135 A | 9/1994 | Isobe et al. |
| 5,368,549 A | 11/1994 | McVicker |
| 5,383,845 A | 1/1995 | Nebolon |
| 5,397,296 A | 3/1995 | Sydor et al. |
| 5,415,625 A | 5/1995 | Cassford |
| 5,431,623 A | 7/1995 | Rice |
| 5,437,619 A | 8/1995 | Malewicz et al. |
| 5,445,602 A | 8/1995 | Grim et al. |
| 5,449,341 A | 9/1995 | Harris |
| 5,458,565 A | 10/1995 | Tillinghast, III |
| 5,468,219 A | 11/1995 | Crippen |
| 5,472,413 A | 12/1995 | Detty |

(56) References Cited

U.S. PATENT DOCUMENTS

| | | |
|---|---|---|
| 5,474,524 A | 12/1995 | Carey |
| 5,497,513 A | 3/1996 | Arabeyre et al. |
| 5,500,268 A | 3/1996 | Billarant |
| 5,512,039 A | 4/1996 | White |
| 5,513,658 A | 5/1996 | Goseki |
| 5,514,081 A | 5/1996 | Mann |
| 5,527,269 A | 6/1996 | Reithofer |
| 5,540,982 A | 7/1996 | Scholz et al. |
| 5,542,911 A | 8/1996 | Cassford et al. |
| 5,562,605 A | 10/1996 | Taylor |
| 5,599,288 A | 2/1997 | Shirley et al. |
| 5,695,452 A | 2/1997 | Grim et al. |
| 5,614,045 A | 3/1997 | Billarant |
| 5,624,389 A | 4/1997 | Zepf |
| 5,635,201 A | 6/1997 | Fabo |
| 5,638,588 A | 6/1997 | Jungkind |
| 5,654,070 A | 8/1997 | Billarant |
| 5,656,226 A | 8/1997 | McVicker |
| 5,665,449 A | 9/1997 | Billarant |
| 5,681,271 A | 10/1997 | Nelson |
| 5,685,830 A | 11/1997 | Bonutti |
| 5,713,837 A | 2/1998 | Grim et al. |
| D392,877 S | 3/1998 | Eguchi |
| 5,737,854 A | 4/1998 | Sussmann |
| 5,759,167 A | 6/1998 | Shields, Jr. et al. |
| 5,769,808 A | 6/1998 | Matthijs et al. |
| 5,774,902 A | 7/1998 | Gehse |
| 5,795,640 A | 8/1998 | Billarant |
| 5,807,294 A | 9/1998 | Cawley et al. |
| 5,823,931 A | 10/1998 | Gilmour |
| 5,823,981 A | 10/1998 | Grim et al. |
| 5,840,398 A | 11/1998 | Billarant |
| 5,857,988 A | 1/1999 | Shirley |
| 5,857,989 A | 1/1999 | Smith, III |
| 5,865,776 A | 2/1999 | Springs |
| 5,865,777 A | 2/1999 | Detty |
| 5,865,782 A | 2/1999 | Fareed |
| 5,873,848 A | 2/1999 | Fulkerson |
| 5,891,061 A | 4/1999 | Kaiser |
| 5,891,071 A | 4/1999 | Stearns et al. |
| 5,900,303 A | 5/1999 | Billarant |
| 5,916,187 A | 6/1999 | Brill |
| 5,948,707 A | 9/1999 | Crawley et al. |
| 5,971,946 A | 10/1999 | Quinn |
| 6,010,474 A | 1/2000 | Wycoki |
| 6,021,780 A | 2/2000 | Darby |
| 6,022,617 A | 2/2000 | Calkins |
| 6,024,712 A | 2/2000 | Iglesiasa et al. |
| 6,063,048 A | 5/2000 | Bodenschatz et al. |
| 6,110,138 A | 8/2000 | Shirley |
| 6,111,138 A | 8/2000 | Van Wijck et al. |
| 6,129,695 A * | 10/2000 | Peters ............... A41D 13/05 |
| | | 602/61 |
| 6,142,965 A | 11/2000 | Mathewson |
| 6,152,893 A | 11/2000 | Pigg et al. |
| 6,159,583 A | 12/2000 | Calkins |
| 6,250,651 B1 | 6/2001 | Reuss et al. |
| 6,254,554 B1 | 7/2001 | Turtzo |
| 6,267,741 B1 | 7/2001 | Lerman |
| RE37,338 E | 8/2001 | McVicker |
| 6,287,268 B1 | 9/2001 | Gilmour |
| 6,289,558 B1 | 9/2001 | Hammerslag |
| 6,360,404 B1 | 3/2002 | Mudge et al. |
| 6,368,295 B1 | 4/2002 | Lerman |
| 6,402,713 B1 | 6/2002 | Doyle |
| 6,405,731 B1 | 6/2002 | Ching |
| 6,413,232 B1 | 7/2002 | Townsend et al. |
| 6,416,074 B1 | 7/2002 | Maravetz et al. |
| 6,461,318 B2 | 10/2002 | Freeman et al. |
| 6,485,776 B2 | 11/2002 | Janusson et al. |
| 6,520,926 B2 | 2/2003 | Hall |
| 6,540,703 B1 | 4/2003 | Lerman |
| 6,540,709 B1 | 4/2003 | Smits |
| D477,409 S | 7/2003 | Mills et al. |
| 6,592,538 B1 | 7/2003 | Hotchkiss et al. |
| 6,592,539 B1 | 7/2003 | Einarsson et al. |
| 6,596,371 B1 | 7/2003 | Billarant et al. |
| 6,598,250 B1 | 7/2003 | Pekar |
| 6,543,158 B2 | 8/2003 | Dieckhaus |
| 6,656,142 B1 | 12/2003 | Lee |
| 6,666,894 B2 | 12/2003 | Perkins et al. |
| 6,689,080 B2 | 2/2004 | Castillo |
| 6,726,641 B2 | 4/2004 | Chiang et al. |
| 6,735,819 B2 | 5/2004 | Iverson et al. |
| 6,740,054 B2 | 5/2004 | Stearns |
| 6,769,155 B2 | 8/2004 | Hess et al. |
| 6,773,411 B1 | 8/2004 | Alvarez |
| 6,861,371 B2 | 3/2005 | Kamikawa et al. |
| 6,861,379 B1 | 3/2005 | Blaszcykiewicz |
| 6,898,804 B2 | 5/2005 | Sandler |
| 6,898,826 B2 | 5/2005 | Draper et al. |
| 6,936,020 B2 | 8/2005 | Davis |
| D519,637 S | 4/2006 | Nordt et al. |
| D519,638 S | 4/2006 | Nordt et al. |
| 7,025,738 B2 | 4/2006 | Hall |
| D520,141 S | 5/2006 | Nordt et al. |
| D521,644 S | 5/2006 | Nordt et al. |
| 7,037,287 B2 | 5/2006 | Cormier et al. |
| 7,150,721 B2 | 12/2006 | Houser |
| 7,161,056 B2 | 1/2007 | Gudnason et al. |
| 7,169,720 B2 | 1/2007 | Etchells et al. |
| 7,198,610 B2 | 4/2007 | Ingimundarson et al. |
| 7,201,728 B2 | 4/2007 | Sterling |
| 7,303,539 B2 | 12/2007 | Binder et al. |
| 7,367,958 B2 | 5/2008 | McBean et al. |
| 7,448,115 B2 | 11/2008 | Howell et al. |
| 7,597,675 B2 | 10/2009 | Ingimundarson et al. |
| 7,698,909 B2 | 4/2010 | Hannula et al. |
| 7,713,225 B2 | 5/2010 | Ingimundarson et al. |
| 7,749,183 B2 | 7/2010 | Ingimundarson et al. |
| 7,762,973 B2 | 7/2010 | Einarsson et al. |
| 7,794,418 B2 | 9/2010 | Ingimundarson et al. |
| 7,806,842 B2 | 10/2010 | Stevenson et al. |
| 7,867,183 B2 * | 1/2011 | Kazmierczak ........ A61F 5/0123 |
| | | 602/23 |
| 7,874,996 B2 | 1/2011 | Weinstein et al. |
| 7,905,851 B1 | 3/2011 | Bledsoe |
| 7,937,973 B2 | 5/2011 | Sorensen et al. |
| 8,016,781 B2 | 9/2011 | Ingimundarson et al. |
| 8,043,244 B2 | 10/2011 | Einarsson et al. |
| 8,216,170 B2 | 7/2012 | Ingimundarson et al. |
| 8,241,234 B2 | 8/2012 | Ingimundarson et al. |
| 8,257,293 B2 | 9/2012 | Ingimundarson et al. |
| 8,267,879 B2 | 9/2012 | Ingimundarson et al. |
| 8,277,401 B2 | 10/2012 | Hammerslag et al. |
| 8,302,269 B2 * | 11/2012 | Pitman ................... A41F 1/006 |
| | | 24/591.1 |
| 8,328,746 B2 | 12/2012 | Ingimundarson et al. |
| 8,328,747 B2 | 12/2012 | Matsunaga |
| 8,425,441 B2 | 4/2013 | Ingimundarson |
| 8,556,783 B1 | 10/2013 | Ihli et al. |
| 8,585,623 B2 | 11/2013 | Ingimundarson |
| 8,745,829 B2 * | 6/2014 | Wanzenboeck ......... A41F 1/006 |
| | | 2/338 |
| 8,864,692 B2 | 10/2014 | Ingimundarson et al. |
| 9,220,622 B2 | 12/2015 | Ingimundarson et al. |
| 9,265,644 B2 | 2/2016 | Einarsson et al. |
| 9,265,645 B2 | 2/2016 | Ingimundarson et al. |
| 9,358,146 B2 | 6/2016 | Thorsteinsdottir et al. |
| 9,364,365 B2 | 6/2016 | Omarsson et al. |
| 9,375,341 B2 | 6/2016 | Ingimundarson et al. |
| 9,474,334 B2 | 10/2016 | Jonsson et al. |
| 9,498,025 B2 | 11/2016 | Omarsson et al. |
| 9,814,615 B2 | 11/2017 | Ingimundarson |
| 2001/0020143 A1 | 9/2001 | Stark et al. |
| 2001/0056251 A1 | 12/2001 | Peters |
| 2002/0032397 A1 | 3/2002 | Coligado |
| 2002/0077574 A1 | 6/2002 | Gildersleeve et al. |
| 2002/0082542 A1 | 6/2002 | Hall |
| 2002/0095750 A1 | 7/2002 | Hammerslag |
| 2002/0107464 A1 | 8/2002 | Castillo |
| 2002/0132086 A1 | 9/2002 | Su-Tuan |
| 2003/0032907 A1 | 2/2003 | Prahl |
| 2003/0069531 A1 | 4/2003 | Hall |

(56) References Cited

U.S. PATENT DOCUMENTS

| | | |
|---|---|---|
| 2003/0204156 A1 | 10/2003 | Nelson et al. |
| 2004/0002674 A1 | 1/2004 | Sterling |
| 2004/0054311 A1 | 2/2004 | Sterling |
| 2004/0058102 A1 | 3/2004 | Baychar |
| 2004/0137178 A1 | 7/2004 | Janusson et al. |
| 2004/0137192 A1 | 7/2004 | McVicker |
| 2004/0153016 A1 | 8/2004 | Salmon et al. |
| 2004/0176715 A1 | 9/2004 | Nelson |
| 2004/0199095 A1 | 10/2004 | Frangi |
| 2004/0225245 A1 | 11/2004 | Nelson |
| 2004/0267179 A1 | 12/2004 | Lerman |
| 2005/0020951 A1 | 1/2005 | Gaylord et al. |
| 2005/0038367 A1 | 2/2005 | McCormick et al. |
| 2005/0081339 A1 | 4/2005 | Sakabayashi |
| 2005/0159691 A1 | 7/2005 | Turrini et al. |
| 2005/0160627 A1 | 7/2005 | Dalgaard et al. |
| 2005/0273025 A1 | 12/2005 | Houser |
| 2006/0015980 A1 | 1/2006 | Nordt, III et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0084899 A1 | 4/2006 | Verkade et al. |
| 2006/0090806 A1 | 5/2006 | Friedline et al. |
| 2006/0094999 A1 | 5/2006 | Cropper |
| 2006/0116619 A1 | 6/2006 | Weinstein et al. |
| 2006/0135900 A1 | 6/2006 | Ingimundarson et al. |
| 2006/0135902 A1 | 6/2006 | Ingimundarson et al. |
| 2006/0135903 A1 | 6/2006 | Ingimundarson et al. |
| 2006/0155229 A1 | 7/2006 | Ceriani et al. |
| 2006/0156517 A1 | 7/2006 | Hammerslag et al. |
| 2006/0191110 A1 | 8/2006 | Howell et al. |
| 2007/0083136 A1 | 4/2007 | Einarsson |
| 2007/0106191 A1 | 5/2007 | Mueller et al. |
| 2007/0130665 A1 | 6/2007 | Wang |
| 2007/0167892 A1 | 7/2007 | Gramza et al. |
| 2007/0167895 A1 | 7/2007 | Gramaza et al. |
| 2007/0185425 A1 | 8/2007 | Einarsson et al. |
| 2007/0225824 A1 | 9/2007 | Einarsson |
| 2008/0034459 A1 | 2/2008 | Nordt, III et al. |
| 2008/0066272 A1 | 3/2008 | Hammerslag et al. |
| 2008/0195014 A1 | 8/2008 | Ingimundarson et al. |
| 2008/0229556 A1 | 9/2008 | Hammer |
| 2008/0294079 A1 | 11/2008 | Sterling et al. |
| 2009/0099562 A1 | 4/2009 | Ingimundarson et al. |
| 2009/0126413 A1 | 5/2009 | Sorensen et al. |
| 2010/0068464 A1 | 3/2010 | Meyer |
| 2010/0125231 A1 | 5/2010 | Knecht |
| 2011/0057466 A1 | 3/2011 | Sachee et al. |
| 2011/0275970 A1 | 11/2011 | Paulos et al. |
| 2012/0010547 A1 | 1/2012 | Hinds |
| 2012/0046585 A1 | 2/2012 | Lee et al. |
| 2012/0090624 A1 | 4/2012 | Chang |
| 2012/0109031 A1 | 5/2012 | Vollbrecht et al. |
| 2012/0220910 A1 | 8/2012 | Gaylord et al. |
| 2013/0184628 A1 | 7/2013 | Ingimundarson et al. |
| 2013/0245523 A1 | 9/2013 | Romo |
| 2014/0121579 A1 | 5/2014 | Hinds |
| 2014/0137314 A1* | 5/2014 | Needham ............ A41F 19/005 2/336 |
| 2014/0194801 A1 | 7/2014 | Ingimundarson et al. |
| 2014/0213947 A1* | 7/2014 | Omarsson ............ A61F 5/0106 602/16 |
| 2014/0214016 A1 | 7/2014 | Ingimundarson et al. |
| 2014/0257158 A1 | 9/2014 | Lee et al. |
| 2015/0032041 A1 | 1/2015 | Ingimundarson et al. |
| 2015/0290014 A1 | 10/2015 | Anglada et al. |
| 2016/0193066 A1 | 7/2016 | Albertsson et al. |
| 2016/0242945 A1 | 8/2016 | Thorsetinsdottir et al. |
| 2016/0278959 A1 | 9/2016 | Omarsson et al. |
| 2016/0296360 A1 | 10/2016 | Ingimundarson et al. |
| 2017/0007435 A1 | 1/2017 | Klutts |
| 2017/0065037 A1 | 3/2017 | Omarsson et al. |
| 2017/0348131 A1 | 12/2017 | Petursson |

FOREIGN PATENT DOCUMENTS

| | | |
|---|---|---|
| DE | 100 04 561 A1 | 8/2001 |
| DE | 20 2004 012 892 U1 | 10/2004 |
| EP | 0 050 769 A1 | 5/1985 |
| EP | 0 196 204 A2 | 10/1986 |
| EP | 0 611 069 A | 8/1994 |
| EP | 1016351 A1 | 7/2000 |
| EP | 2612624 A1 | 7/2013 |
| EP | 2612626 A1 | 7/2013 |
| FR | 2 399 811 A1 | 3/1979 |
| FR | 2 553 996 A1 | 5/1985 |
| FR | 2 766 359 A1 | 1/1999 |
| GB | 1209413 A | 10/1970 |
| GB | 2 136 294 A | 9/1984 |
| GB | 2 455 972 A | 7/2009 |
| JP | H1056932 A | 3/1998 |
| WO | 88/01855 A1 | 3/1988 |
| WO | 94/00082 A1 | 1/1994 |
| WO | 00/49982 A1 | 8/2000 |
| WO | 00/70984 A1 | 11/2000 |
| WO | 2006/015599 A1 | 2/2006 |
| WO | 2006/069221 A2 | 6/2006 |
| WO | 2006/069222 A2 | 6/2006 |
| WO | 2008/115376 A1 | 9/2008 |
| WO | 2009052031 A1 | 4/2009 |
| WO | 2010/117749 A2 | 10/2010 |
| WO | 2011/073803 A2 | 6/2011 |
| WO | 2017019485 A1 | 2/2017 |

OTHER PUBLICATIONS

Advertising Brochure: "NUKO Camp", 6 pages, Camp International, Inc. Jackson, MI (1984).

Advertising Brochure: "Lerman Multi-Ligaments Knee Control Orthosis", 2 pages, Zinco Industries, Inc. of Montrose, CA (1985).

"Information on Flexible Polyurethane Foam", In Touch, vol. 4, No. 3, Jul. 1994, 5 pages.

Advertisement: "Custom Engineered Fabrics and Products for Advanced High Performance", 1 page, Gehring Textiles (visited Dec. 15, 2005), http://www.gehringtextiles.com/d3.html.

Article: "Osteoarthritis of the Knee: An Information Booklet", Arthritis Research Campaign (visited Dec. 14, 2004) http://www.arc.org.uk/about_arth/booklets/6027/6027.htm.

Advertising Brochure: "Freedom to Perform-Fusion", 5 pages, (2005).

Advertising Brochure: "Fusion", 6 pages, Breg, Inc. of Vista, CA (2005).

Advertising Brochure: "Fusion XT", 2 pages, Breg, Inc. of Vista, CA (2005).

Advertising Brochure: "Anderson Knee Stabler", 4 pages, Omni Scientific, Inc. of Lafayette, CA. Feb. 7, 2013.

Advertising Brochure: "OTI Brace", 4 pages, Orthopedic Technology, Inc. of San Leandro, CA. Feb. 7, 2013.

Advertising Brochure: "The Four Axioms of Functional Bracing", 2 pages, Bledsoe by Medical Technology, Inc. (2005).

Advertising Brochure: "The Leader in Knee Motion Management,"8 pages. Donjoy, Carsbad, CA. Feb. 7, 2013.

Advertising Brochure: "The Lenox Hill Lightweight", 1page, Lenox Hill Brace, Inc., New York, NY. Feb. 7, 2013.

Advertising Brochure: "XCL System", 2 pages, Innovation Sports of Foothill Ranch, CA. Feb. 7, 2013.

Advertising Brochure: "The 9 Innovations of the Axiom Custom Brace", 1 page, Bledsoe, Medical Technology, Inc. (2005).

Technical Manual: Bellacure: Restore Your Lifestyle, 10 pages, Bellacure, Inc. (2005).

Technical Manual: "Boa Technology", 3 pages, Boa Technology, Inc. of Steamboat Springs, CO, Feb. 7, 2013.

(56) References Cited

OTHER PUBLICATIONS

Advertising Brochure: "GII Unloader Select", 2 pagse, Ossur HF of Reykjavik, Iceland (visited Mar. 8, 2005), http://www.ossur.com/pring.asp?pageID=1729.

Advertisement: "McDavid Knee Guard and 155 Ligament Augmentation System", 3 pages, Advanced Brace of Irving TX (visited Mar. 8, 2005), http://www.supports4u.com/mcdavid/kneeguard.htm.

Advertisement: "Triax", 1 page, Lanxess AG (visited Mar. 8, 2005), http://www.techcenter.lanxess.com/sty/emea/en/products/description/57/index/jsp?print=true&pid-57.

Reference: "Anatomical Planes", 1 page, (visited Mar. 26, 2005), http://www.spineuniverse.com/displayarticle.phpo/article1023.html.

Advertisement: "M2 Inc. Parts Catalog", 3 pages, M2 Inc. of Winooski, VT (visited Mar. 29, 2005), http://www.m2intl.com/medical.MedClsr.htm.

Advertisement: "Axiom", 3 pages, Bledsoe by Medical Technology, Inc. (visited Jun. 15, 2005), http://www.bledsoebrace.com/custom/axiom.asp.

Advertisement: "Bellacure: The Treatment Device", 6 pages, Bellacure, Inc. (visited Jan. 5, 2006), http://www.bellacure.com/products/index/html.

Advertisement: "Lerman 3-Point Knee Orthosis", 2 pages, Becker Orthopedic of Troy, MI (visited Feb. 26, 2006), http://www.beckerortho.com/knee/3-point/htm.

Article: "Thermoplastic Elastomers TPE, TPR, TPV", 6 pages (visited Mar. 14, 2007), http://www.bpf.co.uk.bpfindustry/plastics_thermplasrubber_TBR.cfm.

International Search Report from PCT Application No. PCT/US2018/054820, dated Feb. 8, 2019.

International Search Report from PCT Application No. PCT/US2017/036073, dated Nov. 22, 2017.

"VELSTICK semi-rigid FASTENER Furnished in Separate, Mating Components", VELCRO Fasteners, Spaenaur, Sep. 2, 2009, 1 Page.

* cited by examiner

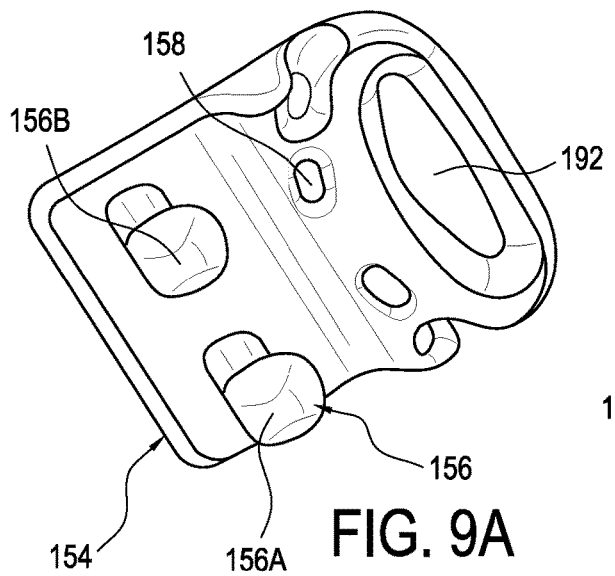
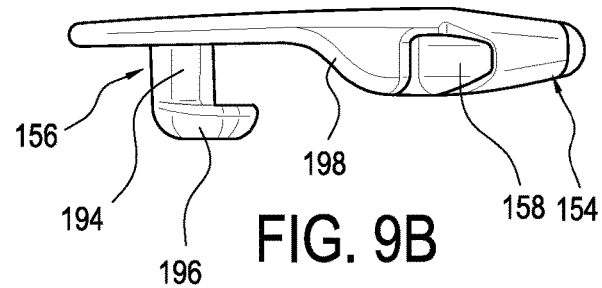
FIG. 9A    FIG. 9B
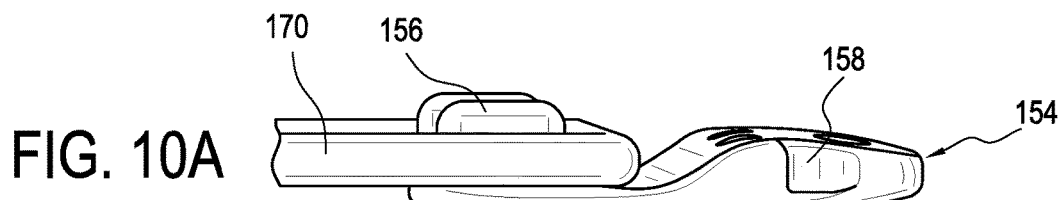
FIG. 10A
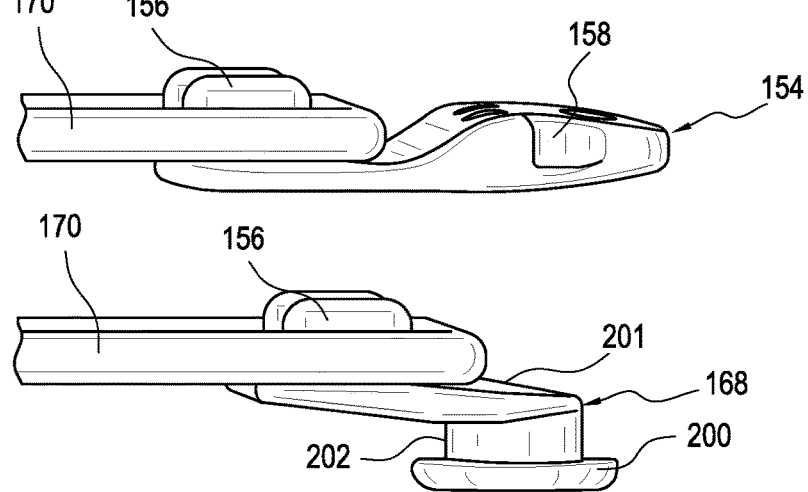
FIG. 10B
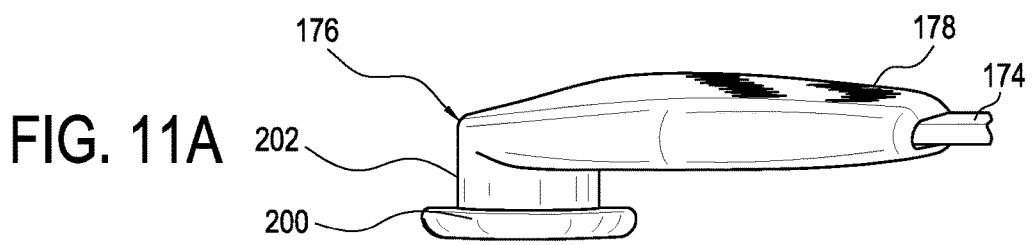
FIG. 11A
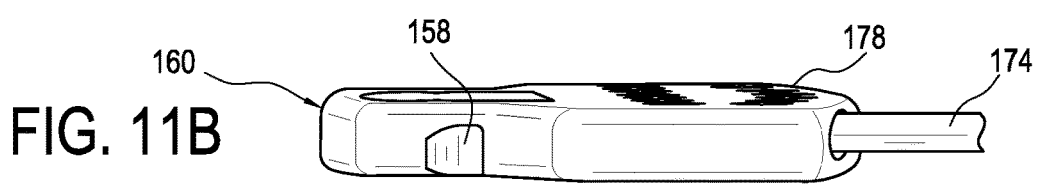
FIG. 11B

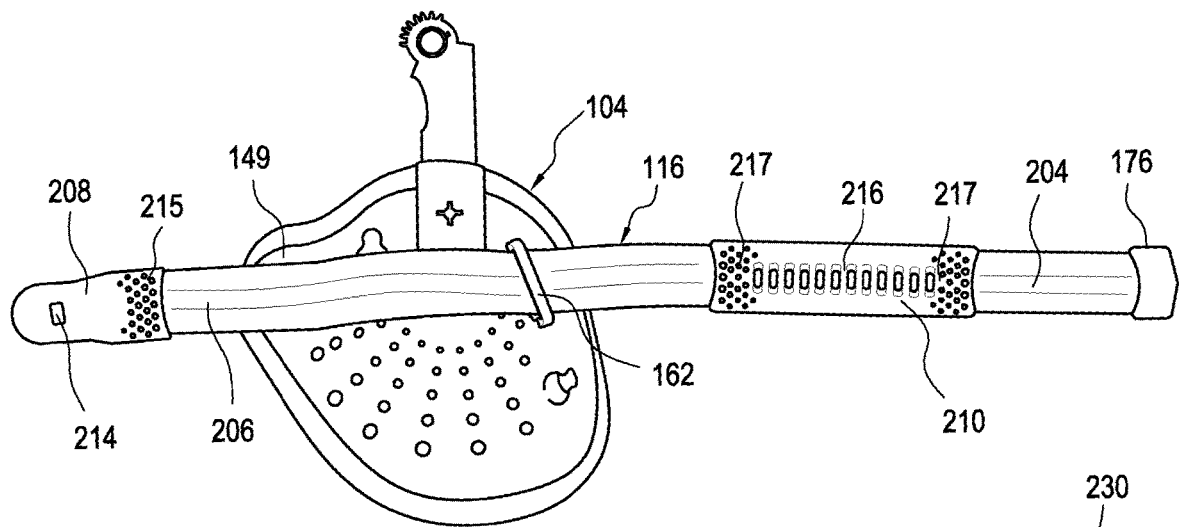
FIG. 12D
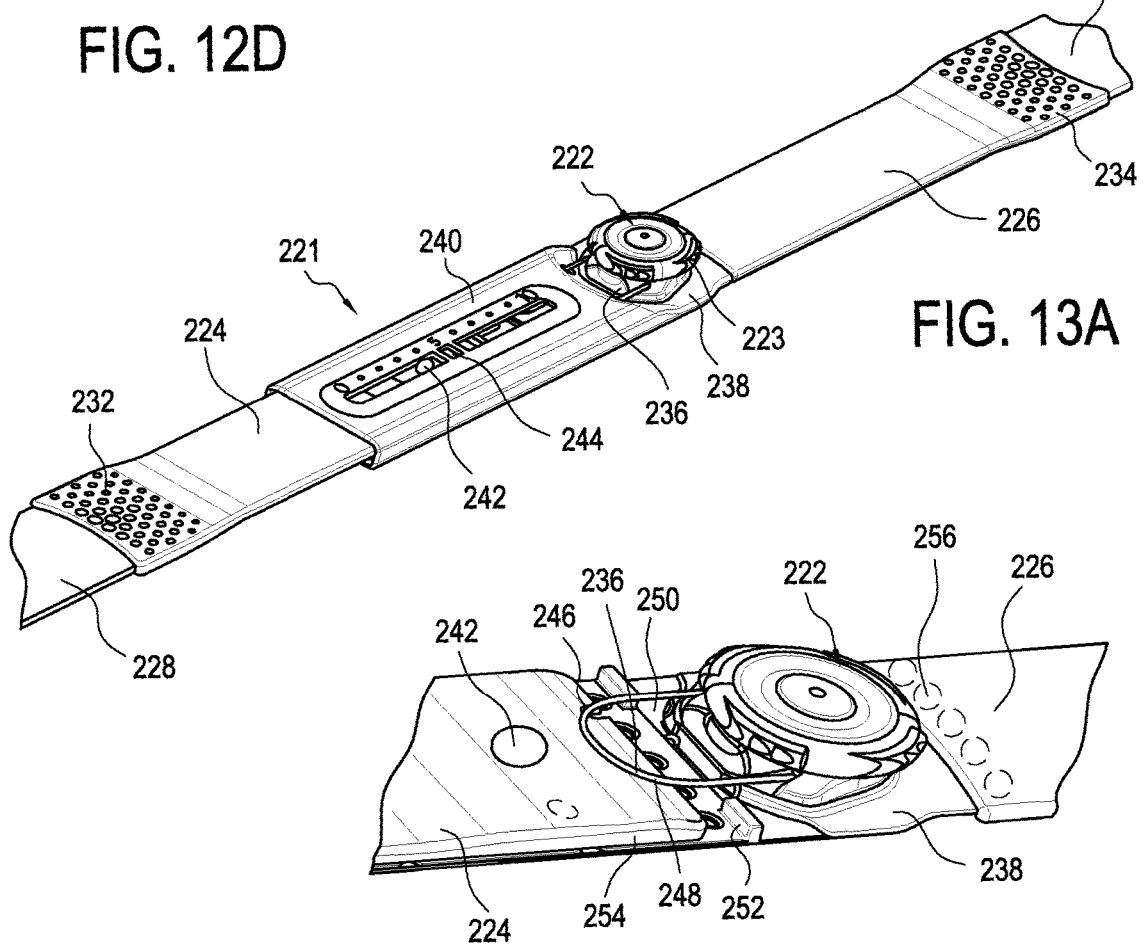
FIG. 13A
FIG. 13B

ORTHOPEDIC DEVICE, STRAP SYSTEM AND METHOD FOR SECURING THE SAME

FIELD OF THE DISCLOSURE

The present disclosure relates to an orthopedic device and corresponding strap systems, and more particularly to an orthopedic device that provides stability, protection, support, rehabilitation, and/or unloading to a portion of the human anatomy in a streamlined, comfortable and light manner.

BACKGROUND

Known orthopedic devices are used for providing stability, protection, support, rehabilitation and/or unloading of a portion of the human anatomy. These known devices, however, are often considered as being uncomfortable, physically bulky, heavy, not durable, tedious and/or difficult to adjust, and costly, requiring numerous manufacturing processes to be produced.

An example of an orthopedic device is a knee brace. As is well understood, knee braces are widely used to treat many knee infirmities. Such braces may be configured to impart forces or leverage on the limbs surrounding the knee joint to relieve compressive forces within a portion of the knee joint, or to reduce the load on that portion of the knee. If knee ligaments are weak and infirm, a knee brace may stabilize, protect, support, unload, and/or rehabilitate the knee.

The knee is acknowledged as one of the weakest joints in the body and serves as the articulating joint between the thigh and calf muscle groups. The knee is held together primarily by small but powerful ligaments. A healthy knee has an even distribution of pressure in both its medial and lateral compartments. It is normal for a person with a healthy knee to place a varus moment on the knee when standing so pressure between the medial and lateral compartments is uneven but still natural.

Knee instability arising out of cartilage damage, ligament strain, and other causes is relatively commonplace since the knee joint is subjected to significant loads during the course of almost any physical activity requiring legs.

Compartmental osteoarthritis is a problematic knee infirmity. It may arise when there is a persistent uneven distribution of pressure in one of the medial and lateral compartments of the knee. Compartmental osteoarthritis can be caused by injury, obesity, misalignment of the knee, or due to aging of the knee. A major problem resulting from osteoarthritis is that smooth cartilage lining the inside of the knee wears away. This leads to a narrowing of the joint space due to the development of cysts and erosions in the bone ends. Because of the narrowing of the joint, bone comes directly in contact with bone, and an uneven distribution of pressure develops across the knee, which may cause the formation of bone spurs around the joint. These changes ultimately lead to increasing pain and stiffness of the joint.

While there are no cures to osteoarthritis, there are many treatments. Individuals with a diagnosis of isolated lateral or medial compartmental osteoarthritis of the knee are confronted with many treatment options such as medications, surgery, and nonsurgical interventions. Nonsurgical interventions include using canes, lateral shoe wedges, and knee braces.

Meniscal tears, or tears in the meniscus, are another common knee ailment that impede proper knee function. These meniscal tears are frequently remedied through partial meniscectomy, which is one of the most common orthopedic procedures in the U.S. as about a ⅓ of men older than 50 have asymptomatic meniscal tears. Acute tears may be treated conservatively, and recent evidence suggest that surgery, including partial meniscectomy, may be unnecessary for degenerative tears. Non-surgical treatment of meniscal tears may involve a period of non/reduced weight bearing.

Degenerative tears are often associated with osteoarthritis changes in the knee. Osteoarthritis and degenerative meniscal tears share many of the same risk factors and biological processes. It may difficult to ascertain if one condition precedes the other, or they occur independently or simultaneously.

Knee bracing is useful in providing compartment pain relief resulting from osteoarthritis and/or meniscal tears by reducing the load on the injured meniscus or tear, and/or knee compartment through applying an opposing external valgus or varus moment about the knee joint. Unloading knee braces have been shown to significantly reduce osteoarthritis knee pain while improving knee function. While known knee braces succeed at reducing pain or at stabilizing a knee joint, many users find these braces to be bulky, difficult to don, complicated to configure and/or adjust, not durable, and uncomfortable to wear.

Orthopedic device frames may cause pressure points, be uncomfortable around the edge, have poor breathability, look and feel bulky and/or aesthetically unattractive, be difficult to adjust in shape, and lack durability among other problems.

Strapping systems are commonly used to secure orthopedic devices to the user's anatomy. Few changes have been made to strapping systems, and little focus has been given to improving strapping. Rather, the emphasis in orthopedic devices often relates to the frame structure and methods for preventing migration on the user during use, and strapping systems are typically off-the-shelf products, with little to no focus devoted thereto.

Current strap designs typically involve aggressive hook and loop systems with a tendency to tear soft-good type braces or make it difficult for corresponding areas on a hard frame to maintain hook or loop patches for receiving straps bearing corresponding locking hook or loop. These straps may have a single property regarding elasticity; they are elastic or inelastic, but rarely do they include both elasticities arranged at strategic locations.

Sizing of many current strap designs may allow for severing the length of the strap to fit a user's anatomy at a time, but such strap designs often lack means for lengthening or reducing length, as desired by a user or set by a clinician. Current strap designs do not possess means for quickly attaching and removing the strap systems from a frame of the orthopedic device. As the strap systems are often not given much design consideration, they cause complaints due to discomfort and difficulty of adjustment. They may be formed from nylon or other inexpensive textile materials lacking sufficient pressure distribution or breathability. Such materials can also lack desired durability. There is a need for strap systems that are injection molded and free of textiles. Current straps also lack designs and/or implements to improve durability of the strap itself. Hook and loop fasteners are commonly used for adjusting strap length but can wear out, causing durability issues. Hook and loop fasteners have the additional disadvantage of frequently coming undone during normal use and being imprecise to adjust, making it difficult to ensure a sure fit.

Strap systems and frames may be designed in a way that allows migration of one or more straps along a user's anatomy during use, which migration further adds to discomfort, poor fit, and difficulty of adjustment.

Orthopedic frames and strap systems may be adjustable in size by various means by tensioning a cable, but a problem of the adjustment systems adds bulk and discomfort to the device. Attachments and structures for routing tensioning cables may protrude from one or more shells of the frame, adding bulk, reducing comfort, and reducing durability as the protruding attachments and structures for routing the cables may be more prone to breaking or malfunctioning. There may be too few of such attachments and structures to route the cable, leading to uneven tensioning and/or discomfort. Adjustment systems, such as dial tensioners, may contribute to migration of the frame against the user as the adjustment system is actuated. Cables that terminate on straps rather than within the dial tensioner may reduce durability by causing maintenance problems.

Orthopedic braces, including knee braces, are frequently designed for heavy duty and/or immediate post-operative use, and require of heavy frame elements and robust tensioning elements to severely unload a joint and/or prevent unwanted motion in certain directions to protect a joint. Braces in heavy duty and/or immediate post-operative use that incorporate robust dynamic tensioning straps (and the accompanying adjustment mechanisms) are only suitable and configured for single-strap tensioning. A brace with two or more dynamic tensioning straps, therefore, disadvantageously requires two or more adjustment mechanisms, which increases cost and difficulty of adjustment. There is a need for a transition brace suitable for users in a later stage of recovery, allowing the brace to be lighter in weight and be easier to adjust with a single adjustment mechanism governing multiple dynamic tensioning straps.

There is need of an orthopedic device suitable for treating osteoarthritis and/or meniscal tears and reduces knee pain, improves knee function, reduces compartmental knee loads, and offers ease of application and adjustment while overcoming the problems of existing braces.

SUMMARY

The exemplary embodiments have streamlined features capable of providing relief for degenerative meniscal tears, and/or medial or lateral compartmental osteoarthritis, or functional stability of the knee without the attendant drawbacks of known unloading knee braces. The concepts described with the exemplary knee brace embodiments may be extended to many wearable devices configured to be secured to and/or support numerous portions of anatomy. The embodiments are aimed at improving the life and mobility of affected users by reducing knee pain, improving knee function, reducing compartmental knee loads, and offering ease of application and adjustment.

The exemplary embodiments also include various strap systems that provide versatility in sizing of length, quick and efficient attachment to the frame of the orthopedic device, enhanced durability, improved fit, and enhanced comfort over known strap systems in orthopedic devices.

According to the embodiments of the orthopedic device, as will be evident by the features of the orthopedic and variations thereof, enable an orthopedic device that is easy to apply and adjust, particularly by a single adjustment mechanism for at least two straps. The orthopedic device has a frame, a strap system including first and second straps connecting to the frame, and an adjustment mechanism coupling to the first and second straps, and simultaneously regulating tension in the first and second straps by moving the first and second straps relative to the frame. This provides a substantial advantage over existing single-strap tensioning systems, which make a brace difficult to adjust.

The frame comprises a first shell, a second shell, and a hinge connecting the first and second shells. The first and second straps connect to the first and second shells. First and second struts connect to the hinge and the first and second shells, respectively. The frame is easy to apply and adjust, in part by providing the hinge which is a custom fit hinge in that the struts may be cold-formable, such as by a malleable aluminum. The shells may define channels that protrude from the shell, and through which the struts may be secured to maintain a smooth inner surface of the shells, contributing to the comfort in wearing the brace. The shells may be smaller than in prior orthopedic devices, in part due to a flexible edge area, but also in view of the features, such as the channel formed by the shells. These features allow for a brace that is relatively light-weight and suitable as a transitional brace. The hinge is further strengthened by providing a portion of each strut as part of the hinge; this provides for a stronger hinge without adding greater bulk.

For additional stability, comfort, migration control, and ease of donning and doffing the orthopedic device, a third strap secures to opposed sides of the second shell, extending horizontal or lateral relative to a vertical or longitudinal direction of the orthopedic device.

The first strap may have a first end slidably connecting to the first shell and a second end secured to the second shell. The second strap may have a first end slidably connecting to the first shell and a second end secured to the second shell. The adjustment mechanism may be mounted to the first shell and coupled to first ends of the first and second straps.

To improve ease of adjustment and fit of the orthopedic device, the first shell defines a tension relief slot proximate the adjustment mechanism. The tension relief slot mitigates migration or rotation of the orthopedic device on the user, since adjustment of the adjustment mechanism tensions the straps about the user. The tension relief slot is formed by shell and localizes forces on the shell. The tension relief slot may define an arcuate shape generally matching a shape of the adjustment mechanism. The first shell may form a base for the adjustment mechanism such that the adjustment mechanism is rotatable therein.

At least one of the first and second shells defines a relief zone arranged generally proximate to at least one of the struts. The relief zone may be defined as an arcuate recess along a side of the first or second shell proximate the hinge, and is arranged to mitigate pinching of a user when the orthopedic device is arranged in flexion of the orthopedic device.

A cable having first and second ends is received by the adjustment mechanism, and segments between the first and second ends slidably engage the first and second straps. The first ends of the first and second straps, respectively, are generally oriented in reversed directions relative to one another. The opposed directions of the first ends of the first and second straps may be generally oriented obliquely in non-perpendicular and non-parallel directions relative to a proximal-distal axis of the orthopedic device in an extension configuration.

Like the channel for the struts, the shells may form other features, such as those being molded from and being integrally formed from the shells, as opposed to being attached to shells. Another example of such features can be a plurality of cable guides through which the cable extends. The cable guides may protrude from an outer surface of the shells, and the shells may define a substantially smooth inner surface devoid of protrusions extending therefrom. The inner surface of the shells is preferably smooth so they are comfortable on the wearer, particularly as the shells bend about the anatomy of the user. The cable guides define a plurality of different shaped individual guides. The individual guides may have different shapes such that some guides may be substantially straight, and some guides may be curved or arcuate. A larger number of guides is provided to facilitate better routing of the cable, which results in easier adjustment and a closer fit.

The shell may define a base for an adjustment mechanism to maintain a minimal profile. The adjustment mechanism receives both ends of the cable, which results in easier adjustment and enhanced durability. The ability to adjust both ends of the cable simultaneously enables more consistent tensioning of the straps, and simplifies the process for tightening the straps. It offers a solution to inconsistent tensioning of one strap over the other, and assures that the user does not improperly incur more force on the leg from one strap over the other.

A sleeve extends about and over the first and second shells, and a first and second segments of the first and second straps, respectively, extending over the sleeve between the first and second shells. The sleeve has a stitchless construction, which aids in both comfort and ease in donning and doffing.

Either of the shells may define a shell body, and such shell bodies may define the aforementioned features. A flexible perimeter edge may be secured along a perimeter of the shell body to provide greater comfort to a user. The shell body is preferably formed from a more rigid material than a material formed by the flexible perimeter edge.

In another feature formed by the shells, the shells may define an elongate channel arranged to receive one of the first and second struts. The elongate channel may define a length at least half of a height of the first or second shell. The elongate channel may only protrude from the outer side of one of the first and second shells. At least one of the first and second shells may define an elongate slot and a bar extending over the elongate slot over the outer side, such that the third strap is adapted to extend about the bar. The elongate channel minimizes the profile of the brace and improve durability by providing a more secure connection between the struts and shells.

In another feature defined by the shells, the second shell may define a first keyhole adapted to receive a second end of the second strap. The second shell may define a calf anti-migration portion protruding from a remainder of the second shell. The calf anti-migration portion is generally in correspondence with the second shell channel within the channel length. At least one of the keyholes is located within the calf anti-migration portion. The calf anti-migration feature minimizes migration without comprising comfort or durability.

At least one of the first and second shells may define a plurality of ventilation openings arranged in a pattern. The pattern may be defined as enlarging ventilation openings.

In another feature defined by the shells, the shell bodies may be overmolded with overlay features that advantageously accommodate various features such as struts and straps. The overlay feature provides flexible edges for greater comfort and also receives a terminal of one or more straps. This feature reduces unwanted migration of the strap, improves durability by protecting the strap and the terminal of the strap from damage, and enhances the aesthetic quality of the brace. The same benefits are also afforded to the strut which is received by the overlay features. The overlay can also cover and conceal other features on the shell body, such as cable and/or guides. This also improves durability and comfort.

The straps comprise loop strap material for a soft feel. The straps may include a length adjustment system, and the length adjustment system includes a section having a plurality of openings and a mounting bracket having fasteners selectively engageable with different openings among the plurality of openings. The mounting bracket defines a cable channel for slidably receiving the cable segment. A tab may secure to the first end of the first strap, and the tab defines a cable channel for slidably receiving the cable segment.

In an embodiment of the strap system, the strap system includes an elongate strap having a fixed length, and defines first and second ends. A length adjustment system is connected to the first end of the elongate strap, and the length adjustment system includes a belt segment having a first end secured to the first end of the elongate strap and defines a plurality of openings arranged along a portion of a length of the belt segment to a second end thereof. A bracket is selectively engageable with different opening among the plurality of openings to adjust the length of the length adjustment system.

The belt segment has a first end defining an attachment portion receiving the first end of the elongate strap, and the belt segment may be integrally secured to the first end of the elongate strap. The attachment portion may be molded over the first end of the elongate strap.

The belt segment may define a transition portion proximate the first end and be located adjacent the attachment portion. The transition portion may be defined as a reduced thickness portion extending to the second end of the sleeve. The belt segment may be substantially elastic along its length. The belt segment may trimmable from the second end thereof, thereby enabling a reduction in the plurality of openings. The belt segment may define at least one elongate slot defined between the first end and the plurality of openings.

The at least one elongate slot may extend through the belt segment. The bracket may define a fastener engageable to at least one opening among the plurality of openings. The fastener is preferably defined by an extension portion generally having a length corresponding to a thickness of the belt segment, and a flange portion extending from the extension portion for securing against a surface of the belt segment.

The belt segment may define a plurality of lateral recesses defined between the plurality of openings. The lateral recesses may be defined along and in opposed pairs along inner and outer surfaces of the belt segment.

The length adjustment system of the belt segment defines a plurality of openings, such that each of the openings may form a keyhole shape for receiving a fastener of the mounting bracket. The keyhole shape may define an insertion portion and a locking portion located in a direction of a second of the belt segment opposite of the elongate strap. A seat portion may be defined about the locking portion, and is preferably formed by a recess sized and configured for receiving a flange portion of the mounting bracket.

An anchor bracket is preferably secured to a second end of the strap section. The anchor bracket may define an attachment portion into which the strap section extends and secures. The anchor bracket defines a fastener pin extending therefrom generally perpendicularly to the attachment portion.

The mounting bracket may define an opening at a first end thereof adapted for grasping with a finger for tensioning or pulling the strap. The mounting bracket may define a transition portion located between the fastener and the opening. The transition portion is defined as a tapering between a flattened head portion carrying the fastener and the cable channel and the first end of the mounting bracket. The anchoring bracket defines an anchoring pin and an extension portion extending from a generally flattened body carrying a fastener.

Another embodiment of a strap system comprises a first strap segment having first and second ends, a second strap segment having first and second ends, a buckle secured to the first end of the second strap segment. The buckle preferably carries a pin. A band is preferably secured to the second end of the first strap segment and the second end of the second strap segment. The band forms apertures arranged for securely and removably receiving the pin. The buckle may include a head extending beyond the first end of the second strap segment. The head preferably carries the pin. The second strap segment may form a loop between the first and second ends.

BRIEF DESCRIPTION OF THE DRAWINGS

FIG. 9A is a perspective view of a mounting bracket in the first strap embodiment of FIG. 6A.

FIG. 9B is an elevational detail view of the mounting bracket in FIG. 9A.

FIG. 10A is an elevational detail view of the mounting bracket in FIG. 9A attached to a belt segment.

FIG. 10B is an elevational detail view of an anchor bracket in the first strap embodiment of FIG. 6A.

FIG. 11A is an elevational detail view of an anchor bracket in the strap of FIG. 6B.

FIG. 11B is an elevational detail view of a variation of a mounting bracket, as shown in FIG. 6B.

FIG. 12D is a schematic plan view showing the second shell of FIG. 4 and the third strap embodiment of FIG. 12A.

FIG. 13A is a perspective view of a fourth strap embodiment.

FIG. 13B is a detail view of the adjustment mechanism coupled to the fourth strap embodiment without the sleeve in FIG. 13A.

Figure 1A:
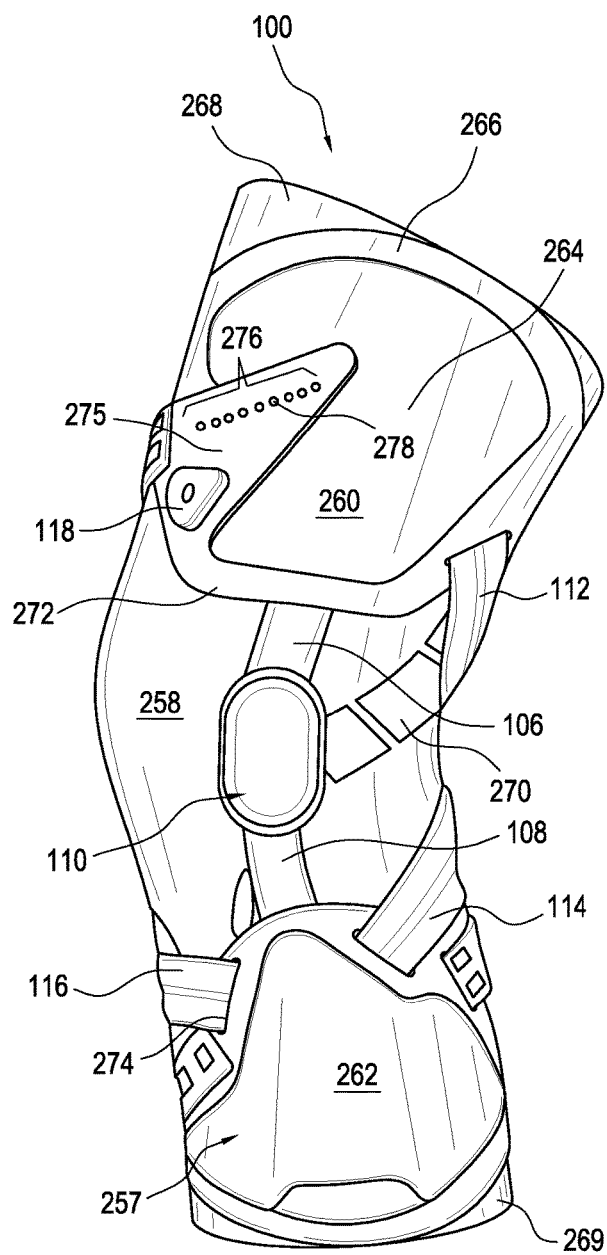
FIG. 1A is a side elevational view of an orthopedic device with a sleeve attached thereto.

The drawing figures are not necessarily drawn to scale, but instead are drawn to provide a better understanding of the components, and are not intended to be limiting in scope, but to provide exemplary illustrations. The figures illustrate exemplary configurations of an orthopedic device, and in no way limit the structures or configurations of an orthopedic device and components according to the present disclosure.

DETAILED DESCRIPTION OF VARIOUS EMBODIMENTS

Figure 1B:
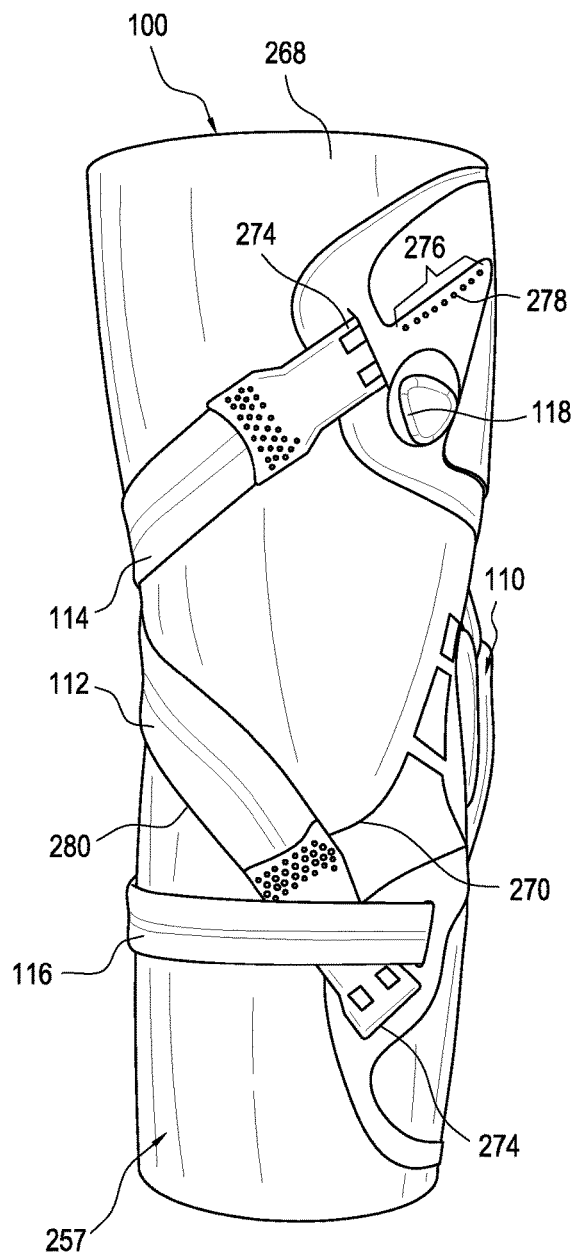
FIG. 1B is a front elevational view of the orthopedic device of FIG. 1A.

As shown in FIGS. 1A and 1B, the orthopedic device 100 is in the form of a knee brace, and builds on the basic description of a knee brace in U.S. Pat. No. 9,358,146, issued on Jun. 7, 2016, incorporated herein by reference. The orthopedic device 100 relates to and functions, at least in part, similarly to the orthopedic device discussed in U.S. Pat. No. 7,198,610, issued on Apr. 3, 2007, and incorporated herein by reference.

Referring to FIGS. 1A and 1B, the orthopedic device 100 is shown with a sleeve 257 connecting and covering the shells described in connection with FIGS. 2-5. The shells are located within first and second pockets 260, 262 formed by the sleeve 257, and inserted externally of the sleeve 257 through openings 272 formed by the pockets 260, 262. The struts 106, 108 and hinge 110 generally extend over the exterior surface of the sleeve 257. The first and second straps 112, 114, and the third strap 116 generally extend over the exterior surface of the sleeve 257, and their engagement with first and second shells occurs within the pockets 260, 262 by entering the pockets 260, 262 by openings 274 so corresponding brackets, pins, and cable are not exposed on the exterior surface of the orthopedic device.

The sleeve 257 includes regions of different material or laminates. The pockets 260, 262 include a pocket material 264, such as Lycra, that extends mostly if not completely about the shells, and is elastic to enable insertion of the shells therein but retains the shells once they are inserted by contracting over such shells. A reinforcement edging 266 surrounds the pockets 260, 262 and serves to reinforce the pocket material 264. The pocket material 264 of the pockets 260, 262 may be the same as sleeve material 258 forming a continuous tubular shape upon which the pockets 260, 262 are formed. The sleeve material 258 is preferably stretchable but has resilience to secure and maintain a position over the user's leg without migration.

An interior surface of the sleeve 257, and thus the sleeve material 258, is continuous in that there is no interruption and provides improved comfort to the user. The end portions 268, 269 of the sleeve 257 may be only formed from the sleeve material 258, since the elasticity of the sleeve material 258 may hold the sleeve 257 and orthopedic device 100 on the leg of the user without additional means such as silicone or other frictional materials commonly applied to an interior surface of a sleeve to minimize migration.

The sleeve 257 may have a stitchless construction wherein the pockets are welded onto the sleeve material, and the end portions 268, 269 may be without or only minimal stitching. The generally stitchless construction allows for a more comfortable orthopedic device 100 by removing potentially skin irritating stitching, and facilitating donning and doffing.

Additional reinforcement elements 270, 280 may be provided along the sleeve material 258 to minimize migration of the straps 112, 114, 116 over the surface of the sleeve 257 or minimize wear of the sleeve material 258. The reinforcement elements 270, 280 may be similar to the reinforcement edging 266 and may merge therewith in certain locations. The reinforcement elements 270, 280 may be provided at strategic locations to counteract tensioning of the straps 112, 114, 116 to provide better form fitting over the user's leg. For example, the reinforcement elements 270, 280 may have stretchability less than the sleeve material 258 and impede elasticity of the sleeve 257 at such locations where the reinforcement elements 270, 280 are located.

The reinforcement elements 270, 280 may have additional functional features in additional to providing counteracting or contrasting elasticity. The reinforcement element 270 may form a support area 275 for the adjustment mechanism 118 to prevent bunching or migration of the sleeve material 258, as the adjustment mechanism 118 is actuated. The support area 275 may also form a plurality of openings 276 that show a relative degree of tensioning or travel of the second strap 114 adjusted by the adjustment mechanism 118 by a marker 274 carried by the second strap 114.

Referring to FIGS. 2-5, the orthopedic device 100 includes a first shell 102, a second shell 104, and a hinge 110 connecting the first and second shells 102, 104. A first strap 112 having a first end slidably connects to the first shell 102 and a second end is removably anchored to the second shell 104, and a second strap 114 has a first end slidably connecting to the first shell 102, and a second end removably anchored to the second shell 104. The first and second straps 112, 114 may be "dynamic force" straps, similarly described in U.S. Pat. Nos. 7,198,610 and 9,358,146, for unloading compartmental arthritis of a knee. The dynamic force strap may apply a counteracting force to the adduction moment, and tensions as the leg extends. A third strap 116 securing to opposed sides of the second shell 104 may be included to provide stability over the calf of the user.

The first strap 112 is preferably arranged for having its length defined between attachment points to the first and second shells 102, 104 adjustable linearly. Adjusting the length linearly implies that the length is not reduced by looping the strap over a D-ring or similar bracket or slot, but rather a linear length of the strap between attachment points (i.e., anchor points to both the first and second shells) is reduced.

The orthopedic device 100 includes first and second struts 106, 108 connecting to the hinge 110 and the first and second shells 102, 104, respectively. Both the first and shells 102, 104 define an elongate channel 132, 134 arranged to receive one of the first and second struts 106, 108. The elongate channels 132, 134 are preferably formed by the material forming the shells 102, 104, and may be molded into shape when the shells 102, 104 are formed. Preferably, the struts 106, 108 are slidable into the elongate channels 132, 134 and are securely retained thereby.

The elongate channels 132, 134 are preferably arranged to reduce a length of the struts 106, 108 located between the first and second shells 102, 104 to provide a more streamlined profile of the orthopedic device 100. The elongate channels 132, 134 may define a length at least half of a height 135 of the first or second shell 102, 104, as they are preferably arranged to extend deeper into the shells 102, 104 for providing the more streamlined profile and better secure to the shells 102, 104. The shells 102, 104 may likewise be sized smaller than conventional braces in part due to greater extension of the struts 106, 108 versus their overall length over the shells 102, 104. Consistent with the more streamlined profile and to maintain smooth, flat surfaces on an inner side I of the first and second shells 102, 104, the elongate channels 132, 134 only protrude from the outer side O of the first and second shells 102, 104, thereby providing a smooth inner surface of the shells 102, 104.

Figure 3A:
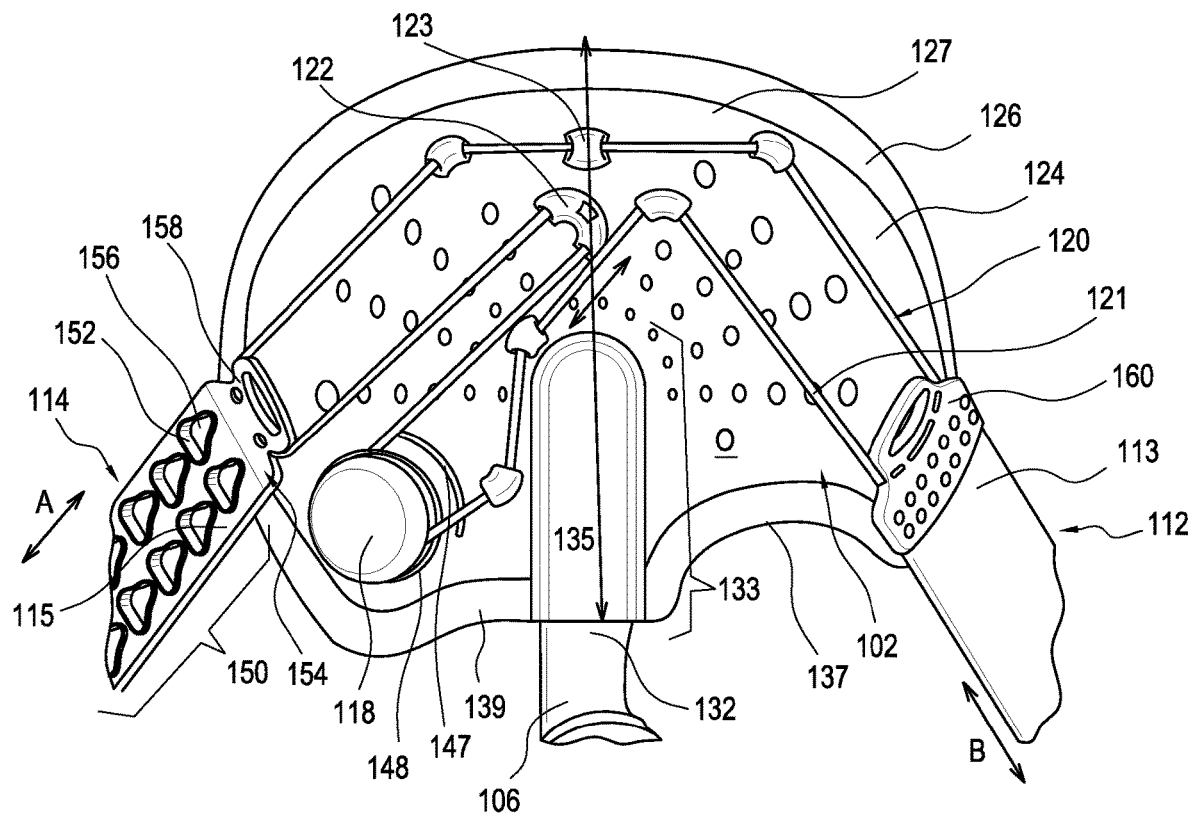
FIG. 3A is a detail view of a first shell in the orthopedic device of FIG. 2.
Figure 3B:
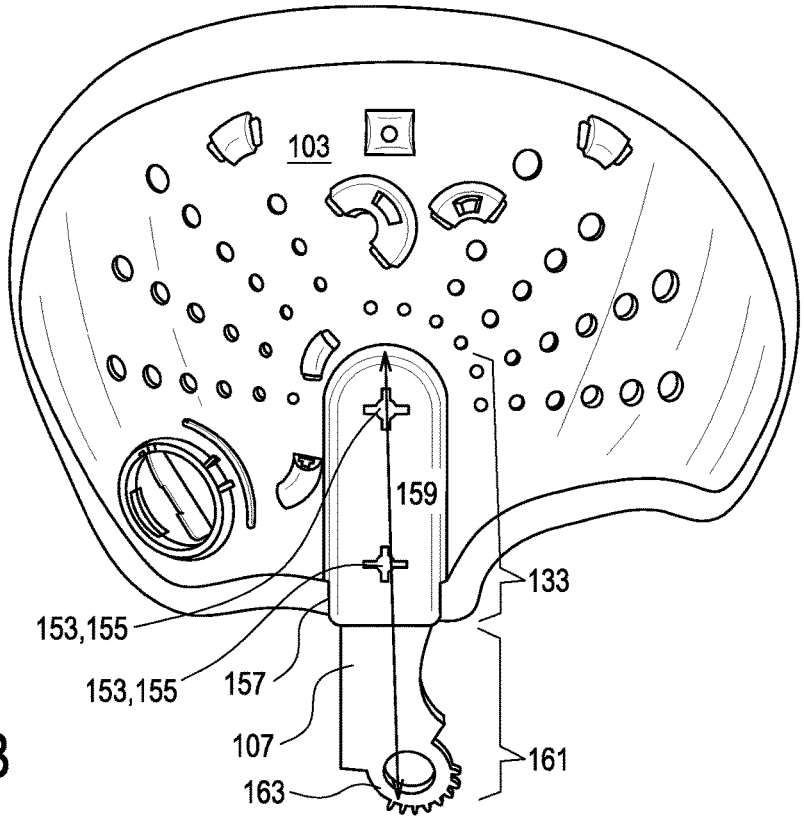
FIG. 3B is a detail view of a variation of the first shell of FIG. 2.

Referring to the variation of first shell 103 in FIG. 3B, the first shell 103 is preferably molded over strut 107 to assure that it interlocks therewith without the necessity of an adhesive or fasteners. Both the first shell 103 and the strut 107 may include alignment holes 153, 155 that allow for the first shell 103 to align with the strut 107 as the first shell 107 is formed. The material of the first shell 103, which is preferably an injection moldable polymeric material such as nylon, may interlock with the strut 107 in that the polymeric material surrounds a periphery of the alignment hole 153 formed by the strut 107, which is metal. The polymeric material of the first shell 103 may therefore extend through the alignment hole 153 of the strut 107, and coat the strut 107 about the periphery of the alignment hole 153. The first shell 103 and the strut 107 may include at least one set of coaxial holes 153, 155, and preferably include at least two sets of coaxial holes 153, 155.

While the interlocking of the first shell 103 to the strut 107 sufficiently holds, if it is desired for greater attachment of the strut 107 to the first shell 103, the first shell 103 likewise includes the alignment hole 155 that aligns with the alignment hole 153 of the strut 107. A fastener (not shown) may extend through the coaxial alignment holes 153, 155 to enhance the attachment of the first shell 103 to the strut 107.

While FIG. 3A exemplifies the channel length 133 to the shell height 135, FIG. 3B exemplifies how the channel 157 may have a greater channel length 133 (as in FIG. 3A) than a length 161 of the strut 107 outside of the channel 157. The length 161 of the strut 107 outside the channel may include a portion of the strut 107 forming a portion 163 of the hinge (not shown). It is not necessary, however, that the strut 107 form a portion 163 of the hinge, although it may aid in stability, reduce parts and provide greater durability to the hinge. The arrangement of the lengths of the shell 103, its channel 157, and the strut 107 enable a simplified hinge arm shape, while providing a more streamlined brace. The struts may be shortened for a sleeker and less bulky shape of the brace, particularly as the shells are generally retained within a sleeve, as shown in FIGS. 1A and 1B.

Figure 4:
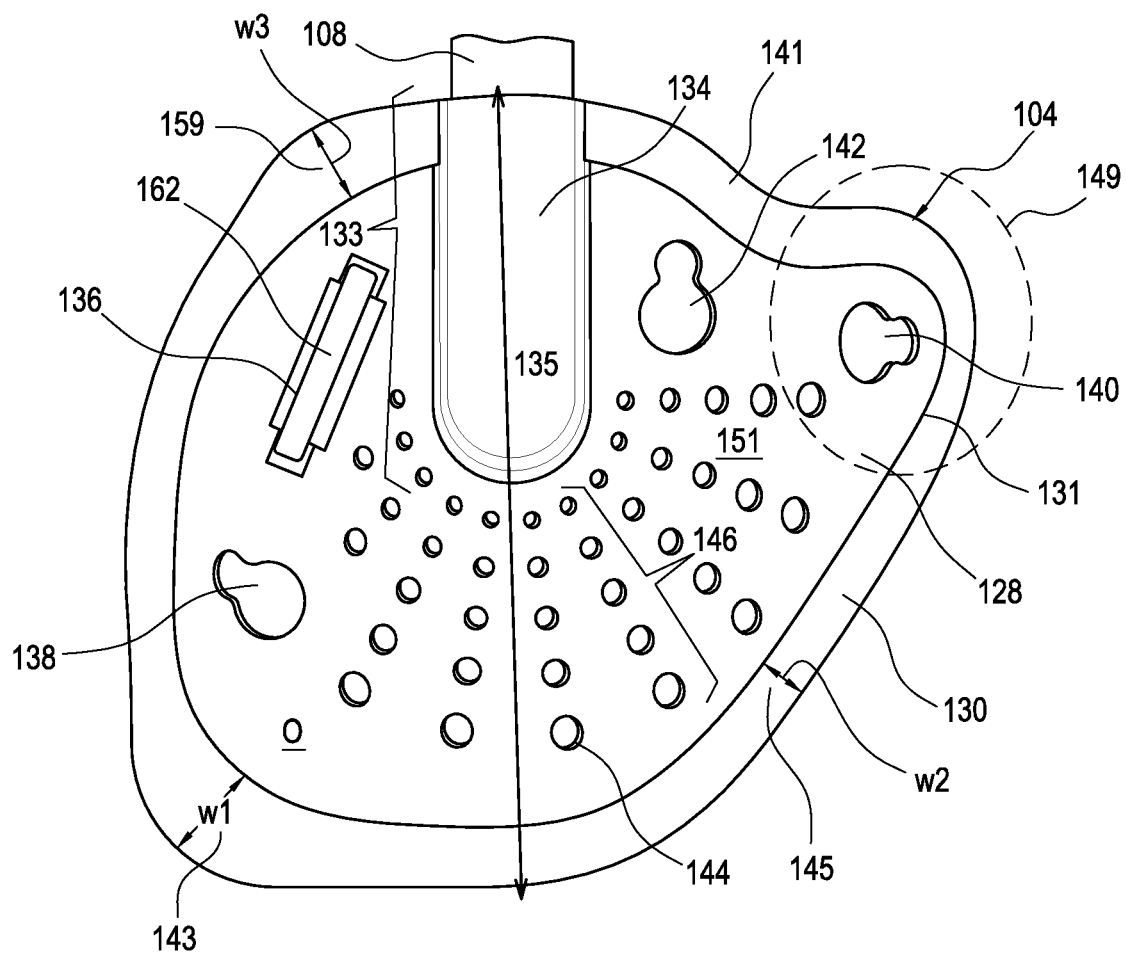
FIG. 4 is a detail view of a second shell in the orthopedic device of FIG. 2.

The first and second shells 102, 104 include shell bodies 124, 128 and flexible perimeter edges 126, 130 secured along perimeters 127, 131 of the shell bodies 124, 128. The shell bodies 124, 128 may be rigid or semi-rigid, thereby maintaining their shape according to movement of the user when or once the orthopedic device 100 is secured onto the user. The flexible perimeter edges 126, 130, alternatively, are flexible upon movement of the user, thereby providing a pressure-relieving edge. The flexible perimeter edges 126, 130 may extend over a substantial entirety of the first and second shells 102, 104, but may be interrupted by the channels 132, 134, as depicted in FIGS. 3A, 3B and 4. The flexible perimeter edge 126, 130 may be formed similarly to the processes described in U.S. Pat. Nos. 7,198,610, and 7,749,183, issued on Jul. 6, 2010, and incorporated by reference.

Referring to FIG. 4, second shell 104 is shown with a flexible perimeter edge 130 having varying first, second, and third widths 143, 145, 159. Widths 143, 145, 159, denoted by w1, w2, and w3, respectively, impart varying degrees of flexibility. The width of the flexible perimeter edges 126, 130 may be uniform around the perimeters 127, 131 of the shell bodies 124, 128, or the width of the flexible perimeter edges 126, 130 may vary according to pre-determined locations about the perimeters 127, 131 of the shell bodies 124, 128. The flexible perimeter edges 126, 130 varying in width according to pre-determined areas, as depicted in FIG. 4, advantageously allows the shell bodies 124, 128 to have varying degrees of flexibility in desired areas, which increases comfort for a user by reducing pressure points.

The second shell 104 defines an anti-migration portion 149 generally in correspondence with the second shell channel 134 within a channel length 133 thereof. The anti-migration portion 149 is arranged to protrude from a remainder 151 of the second shell 104 and is adapted to extend laterally from the second shell remainder 151 and over at least a portion of a calf of the user. The anti-migration portion 149 may include at least one keyhole 140 for receiving a bracket from one of the first and second straps 112, 114, and preferably a keyhole 140 for receiving an end of the third strap 116 adapted to secured over the calf of the user.

The first and second shells 102, 104 define relief zones 137, 139, 141, arranged generally proximate to at least one of the struts 106, 108. The relief zones 137, 139, 141 are defined as an arcuate recess along sides of the first or second shell 102, 104 proximate to the struts 132, 134, and face the hinge 110. The relief zones 137, 139, 141 are generally arcuate in shape and contoured to correspond to anatomy of the leg. The relief zones 137, 139, 141 are provided to mitigate pinching of a user's when the orthopedic device 100 is arranged in flexion. The relief zones 137, 141 are preferably located on the posterior side of the hinge 110 as such areas corresponding to user's leg in full flexion of the orthopedic device 100 are tensioned and prone to tightening.

The first and second shells 102, 104 define a plurality of ventilation openings 144 arranged in a pattern 146 and may be defined as enlarging ventilation openings 144 toward outer perimeters opposite the hinge 110, since these areas correspond to enlarging of the profile of the user's leg away from the knee; for example, as rays of ventilation openings 144 flaring in size toward the outer perimeter. The ventilation openings 144 may cause the first and shells 102, 104 to have greater bendability aside from semi-rigid or rigid characteristics of the material forming the first and second shells 102, 104, thereby better accommodating the leg profile of individual users of the orthopedic device 100.

Figure 5:
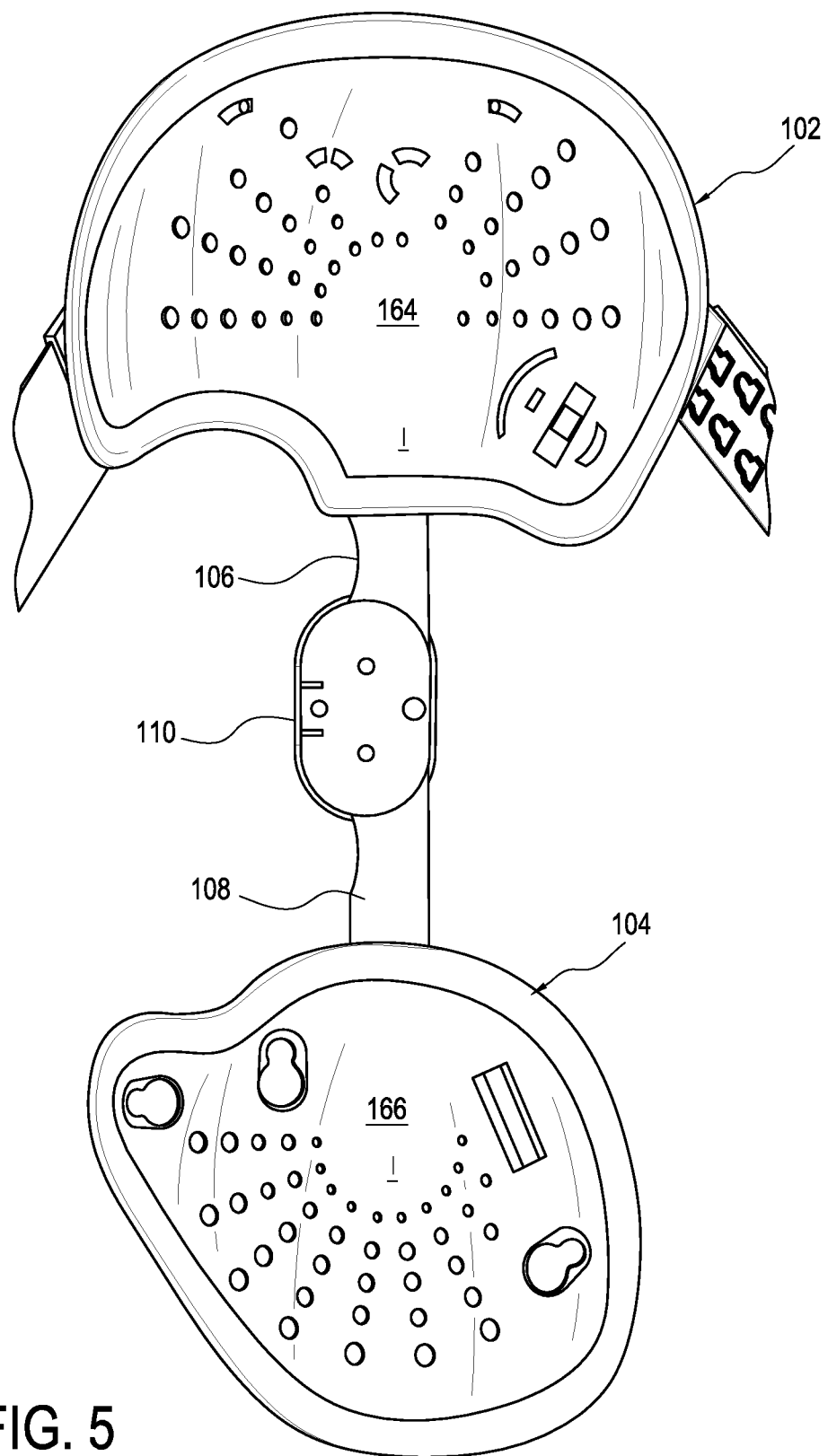
FIG. 5 is an elevational view of an inner side of the orthopedic device of FIG. 2.

As depicted in FIG. 5, the first and second shells 102, 104 define substantially smooth inner surfaces 164, 166 devoid of protrusions extending therefrom. The inner surfaces 164, 166, in combination with spacer material or other suitable padding, enables a breathable and lightweight feel for the user, with assistance from the ventilation openings 144.

The second shell 104 defines an elongate slot 136 and a bar 162 extending over the elongate slot 136 over the outer side O of the second shell 104. The third strap 116 is adapted to extend about the bar 162 located at a first side of the second shell and extend to the keyhole 140 on a second side of the second shell 104 to form a circumference in combination with the second shell 104. The third strap 116 is arranged to extend over the anterior leg and over at least a part of the posterior leg, including the user's calf.

Figure 6:
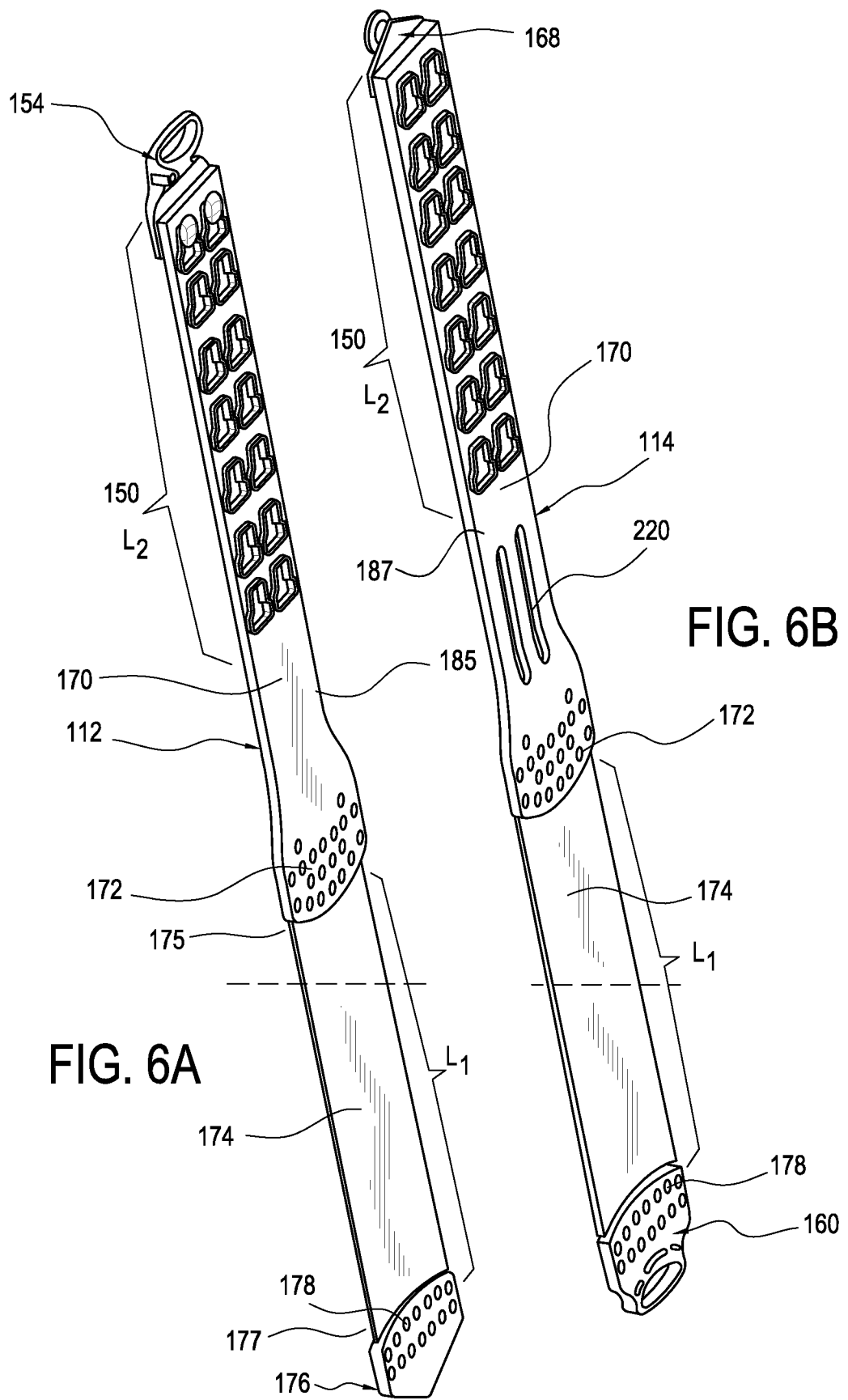
FIG. 6A is a perspective view of a first strap embodiment in the orthopedic device of FIG. 2.
FIG. 6B is a perspective view of a second strap embodiment in the orthopedic device of FIG. 2.

The second shell 104 may include other keyholes 138, 142 for receiving brackets from the first and second straps 112, 114. The second shell 104 defines a first keyhole 138, 140, 142 adapted to receive a second end of the second strap 112. The keyholes 138, 140, 142 may be configured similarly to the locking keyholes formed by the first and second shells 102, 104, and described at least in connection with FIGS. 5 and 6 of U.S. patent application publication 2014/0257158, published on Sep. 11, 2014, and incorporated herein by reference.

An adjustment mechanism 118 is preferably mounted to the first shell 102 and coupled to the first and second straps 112, 114 for simultaneously adjusting the first ends of the first and second 112, 114 straps relative to the first shell 102. To better integrate the adjustment mechanism 118 to the first shell 102 and create a more streamlined profile of the orthopedic device 100, the first shell 102 forms a base 148 for the adjustment mechanism 118 such that the adjustment mechanism 118 is rotatable therein. Such a configuration eliminates the need to add an entire adjustment mechanism to an outer surface of the first shell 102, and thereby reducing bulging of the adjustment mechanism 118 from the first shell 102.

Consistent with the base 148, the first shell 102 defines a tension relief slot 147 proximate the adjustment mechanism 118. The tension relief slot 147 defines an arcuate shape generally matching a shape of the adjustment mechanism 118. The tension relief slot 147 accommodates movement of the adjustment mechanism 118 as is it rotated in the base 148, and mitigates migration of the first shell 102 on the leg of the user as the adjustment mechanism 118 is turned by user.

A cable 120 has first and second ends received by the adjustment mechanism 118, and cable segments 121 between the first and second ends slidably engaging the first and second straps 112, 114. The cable 120 is selectively lengthened by and relative to the adjustment mechanism 118, and unlike in prior art devices, the cable 120 does not terminate on the first shell 102, but rather the ends of the cable 120 terminate within the adjustment mechanism 118. First ends 113, 115 of the first and second straps 112, 114, respectively, are generally oriented in reversed directions A, B relative to one another by the cable segments 121. Specifically, the opposed directions of the first ends 113, 115 of the first and second straps 112, 114 are generally oriented obliquely in non-perpendicular and non-parallel directions relative to a proximal-distal axis of the orthopedic device in an extension configuration.

A plurality of cable guides 122 are preferably formed by the first shell 102 itself rather than being secured to the first shell. The cable guides 122 may only protrude from an outer surface O of the first shell 102, as shown from FIGS. 2, 3 and 5. The cable 120 slidably extends through the cable guides 122 and defines a cable route according to an arrangement of the cable guides 122, which define a plurality of different shaped individual guides 123, 125. At least one individual cable guide 123 is substantially straight, and wherein at least one individual cable guide 125 is arcuate. The first shell 102 may include many more cable guides 122 over the prior art, in part because they are formed directly from the shell body and material thereof. This is advantageous since there is no need to include fasteners for securing the cable guides 122, and thereby adding bulk to the cable guides 122 and the first shell 102.

The first strap 112 includes a length adjustment system 150. According to the embodiments of FIGS. 1-4, the length adjustment system 150 includes a section having a plurality of openings 152 and a mounting bracket 154 having fasteners 156 selectively engageable with different openings among the plurality of openings 152, and enables a unitary strap so the first strap 112 is functionally equivalent among any of the plurality lengths available in view of the selective placement of the mounting bracket 154 among the plurality of openings 152. The mounting bracket 154 preferably defines a cable channel 158 for slidably receiving the cable segment 121. The first strap 112 is adapted to slide along the outer surface O of the first shell 102 according to adjustment of the cable 120 according to adjustment of the adjustment mechanism 118.

The second strap 114 includes a mounting bracket 160 securing to the first end 113 of the second strap 112. The mounting bracket 160 defines a cable channel 158 for slidably receiving the cable segment 121, however the mounting bracket 160 is arranged without being in combination with a length adjustment system 150, and is slidable along the surface of the first shell 102 according to adjustment of the cable 120 according to adjustment of the adjustment mechanism 118.

FIGS. 6A-13B show variations of strap systems that can be used in combination with the orthopedic device of FIGS. 1-5, or in other applications. In each instance, the strap systems employ means which enable and facilitate easy length adjustment. These variations allow for strap systems that avoid the attendant drawbacks of known strap systems, particularly in orthopedic devices, that solely rely on hook and loop fasteners for securing and adjusting straps, and including D-rings or other bulky and heavy brackets used to redirect or mount straps thereto. The variations rely on features that facilitate bending and are formed of materials and configurations that provide greater comfort, contouring and breathability for users.

In an example, the first strap 112 has an adjustable length including an elongate strap 174 having a fixed length L1, and defining first and second ends. A length adjustment system 150 connects to the first end 175 of the elongate strap 174. The length adjustment system 150 includes a belt segment 170 having a first end secured to the first end 175 of the elongate strap 174 and defines a plurality of openings 152 arranged along a portion of a length of the belt segment 170 to a second end 173 thereof. A bracket 154, 168 selectively engages with different openings among the plurality of openings 152 to adjust the length L2 of the length adjustment system 150.

The belt segment 170 has a first end 171 defining an attachment portion 172 receiving the first end 171 of the elongate strap 174. The belt segment 170 is preferably integrally secured to the first end of the elongate strap 174. The attachment portion 172 may be molded over the first end of the elongate strap 174, thereby forming an overmold connection defined by the mixture or melding of the material forming the attachment portion 172 with a material forming the elongate strap 174. The elongate strap 174 may be formed from a polymeric material or a textile, such as a brushed loop material providing superior compressive and breathable properties. The elongate strap 174 may comprise a nylon webbing, or may comprise a soft loop material laminated and sewed with a thin nylon/polyester strap in a center core.

The belt segment 170 defines a transition portion 190 proximate the first end 171 thereof and adjacent the attachment portion 172. The transition portion 190 is formed as a reduced thickness portion extending to the second end 173 of the belt segment 170. The belt segment 170 may be substantially elastic along its length L2, or alternatively may be inelastic yet flexible and resilient to bend according to the anatomy of the user although it may not yield under tension on the user. The belt segment 170 may be trimmable from the second end 177 thereof, thereby enabling a reduction in the plurality of openings 152. The belt segment 170 is preferably a stretchable plastic material arranged to eliminate the need for an elastic element or band to be sewed in the elongate strap 174 and for elastic to be sewed to the bracket 154.

The belt segment 170 defines at the first end 171 a curved end 193 to ease in bending of the elongate strap 174. A plurality of holes 191 are formed by the belt segment 170 at the first end 171 to at least maintain the belt segment 170 in position with the elongate strap 174, if and when the belt segment 170 is molded over the elongate strap 174. The first end 171 of the belt segment 170 is arranged to close tightly around the elongate strap 174 so the material forming the belt segment 170 does not flow out onto the elongate strap 174.

Figure 7:
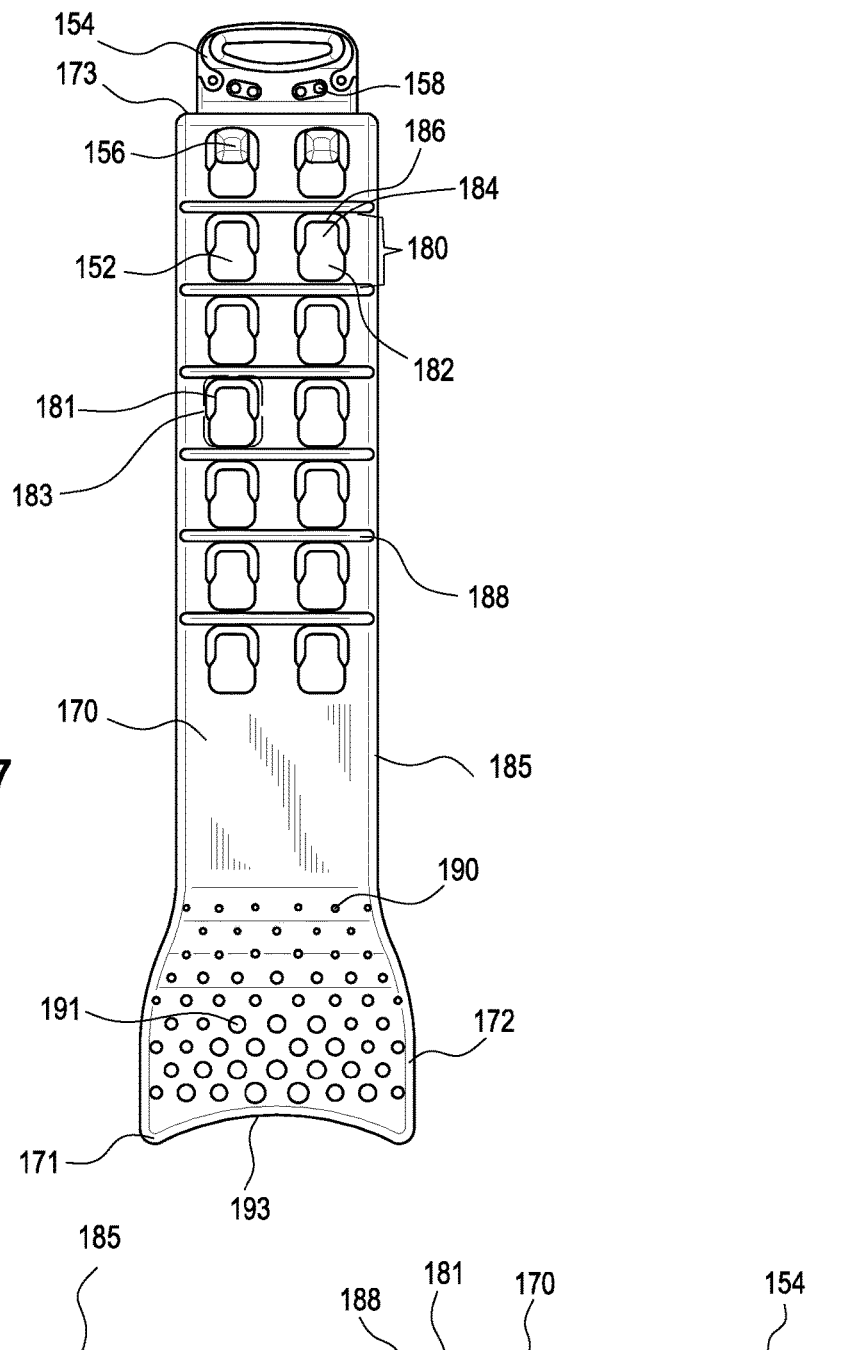
FIG. 7 is a plan view of a length adjustment system of the first strap embodiment in FIG. 6A.
Figure 8:
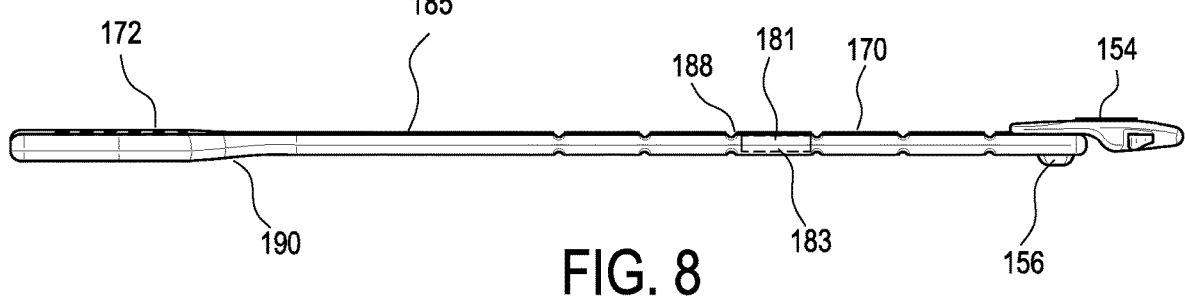
FIG. 8 is an elevational detail view of the length adjustment system of the first strap embodiment in FIG. 6A.

In the embodiment of FIG. 6A, FIG. 7 and FIG. 8, the belt segment 170 defines a legnth 185 between the length adjustment system 150 and the attachment portion 172, which is devoid of openings. In the embodiment of FIG. 6B, the belt segment 170 defines at least one elongate slot 220 defined between the first end 171 and the plurality of openings 152 within a length 187 of the belt segment 170, which facilitates bending of the belt segment 170 and improves breathability of the belt segment 170 against the user as the belt segment 170 may be formed from a polymeric material. The at least one elongate slot 220 may extend completely through the belt segment 170, or may comprise a recessed portion extending from at least one of the sides of the belt segment 170.

FIGS. 6A, 9A, 9B, and 10A show a bracket 154, which serves as a bracket for mounting the aforementioned cable thereto. The bracket 154 includes at least one fastener 156, preferably but not limited to first and second fasteners 156A, 156B, defined by an extension portion 194 generally having a length corresponding to a thickness of the belt segment 170, and a flange portion 196 extending from the extension portion 194 for securing against a surface of the belt segment 170. The mounting bracket 154 defines an opening 192 at a first end thereof adapted for grasping with a finger for tensioning or pulling the strap 112. The bracket 154 defines a transition portion 198 located between the fastener 156 and the opening 192 such that the transition portion 198 is defined as a tapering between a flattened head portion carrying the fastener 156 and the cable channel 158 and the first end of the mounting bracket 154. The transition portion 198 enables the bracket 154 to be arranged at an end portion of the belt segment 170 and overlap its edge at the first end thereof.

FIGS. 6B and 10B show an embodiment of the bracket 168 that defines a fastener 156 engageable to at least one opening among the plurality of openings 152. This bracket 168, which serves as an anchoring bracket to anchor the corresponding strap 114 to one of the first and second shells 102, 104, defines an anchoring pin 200 and an extension portion 202 extending from a generally flattened body 201 carrying a fastener 156. The anchoring pin 200 is adapted to engage to a shell 102, 104 by one of the aforementioned keyholes.

Referring specifically to FIGS. 7 and 8, the belt segment 170 defines a plurality of lateral recesses 188 defined between the plurality of openings 152 for receiving the at least one fastener 156, and are located along and in opposed pairs along inner and outer surfaces of the belt segment 170 to facilitate bending of the belt segment 170.

The belt segment 170 defines a plurality of openings 152, whereby each of the openings preferably forms a keyhole shape 180 for receiving a fastener or anchoring bracket 176 of the mounting bracket 154. The keyhole shape 180 forms an insertion portion 182 and a locking portion 184 located in a direction of a second of the belt segment 170 opposite of the elongate strap 174. A seat portion 186 is defined about the locking portion 184, and is formed by a recess sized and configured for receiving the flange portion 196 of the mounting bracket 154.

The belt segment 170 may be molded over a reinforcing substrate (not shown) with a greater toughness than the belt segment 170, or alternatively the seat portions 186 may comprise individual inserts 181 over which the belt segment is molded. The inserts 181 may have a toughness greater than the belt segment 170. FIGS. 7 and 8 show how each of the inserts 181 preferably have a profile 183 having an outer periphery fully encased or over-molded by the material of the belt segment 170, with an inner periphery of the inserts 181 generally forming the border of the insertion portion 183. The inserts 181 may also be located within or between the lateral recesses 188 so as not to compromise bending and the overall flexibility of the belt segment 170. The inserts 181 may have a color contrast with the belt segment 170, thereby adding visual identification as to where the fasteners 156 may secure.

FIG. 11A depicts a variation of the anchoring bracket 176, and is shown by example in FIG. 6A as being secured to a second end of the strap section 174. The anchoring bracket 176 defines an attachment portion 178 into which the strap section 174 extends and secures. The anchoring bracket 176 has a fastener pin or hook 200 extending therefrom generally perpendicularly to the attachment portion 178.

FIG. 11B depicts a variation of the mounting bracket 160 without the at least one fastener. Both the mounting bracket 160 and the anchoring bracket 176 define a low profile and minimize protruding from the first and second shells. In any of the embodiments of the brackets described herein, the brackets may be modified to include any of the features described herein.

Figure 2:
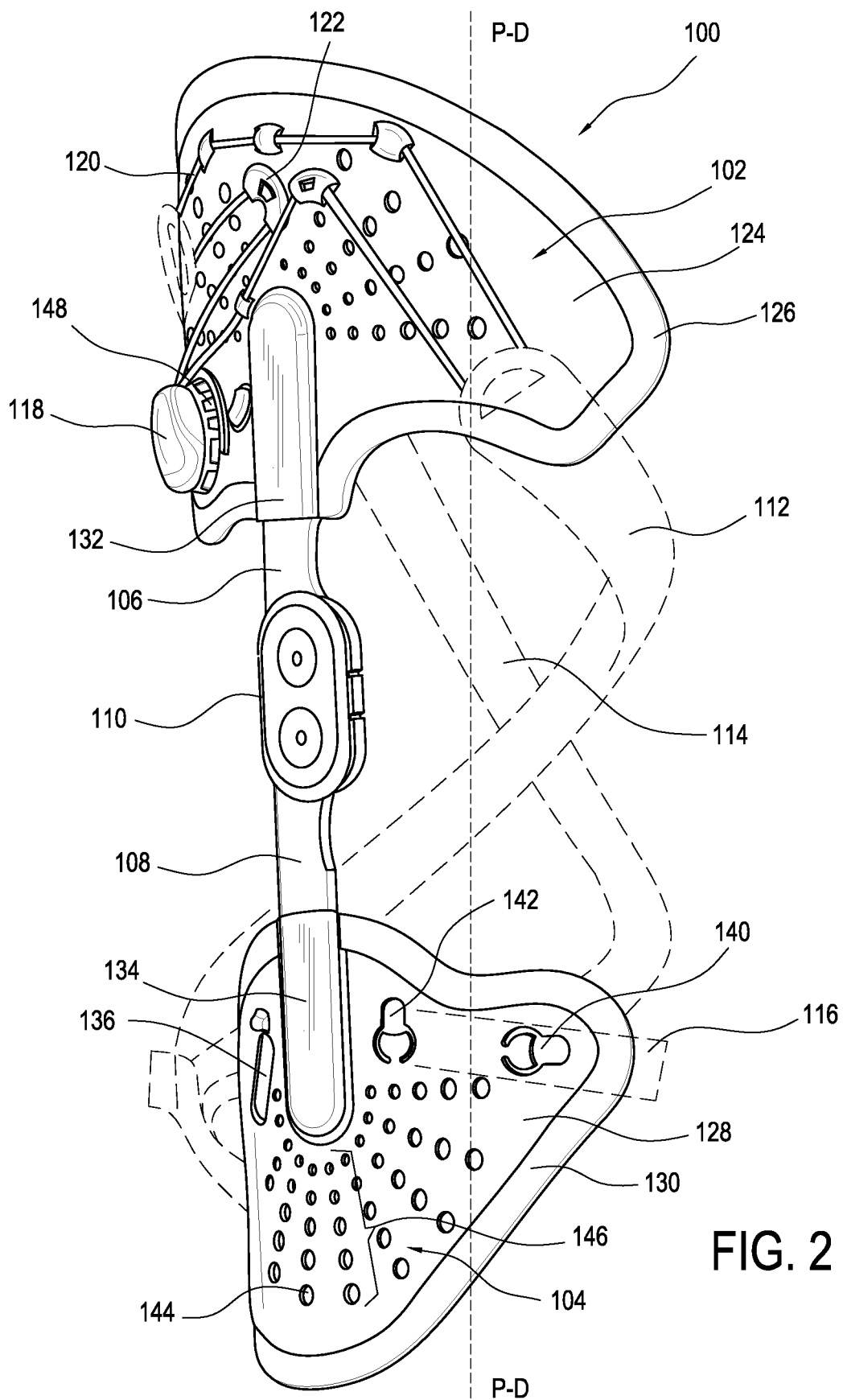
FIG. 2 is a perspective view of an outer side of the orthopedic device of FIG. 1A in an extension configuration without the sleeve.
Figure 12A:
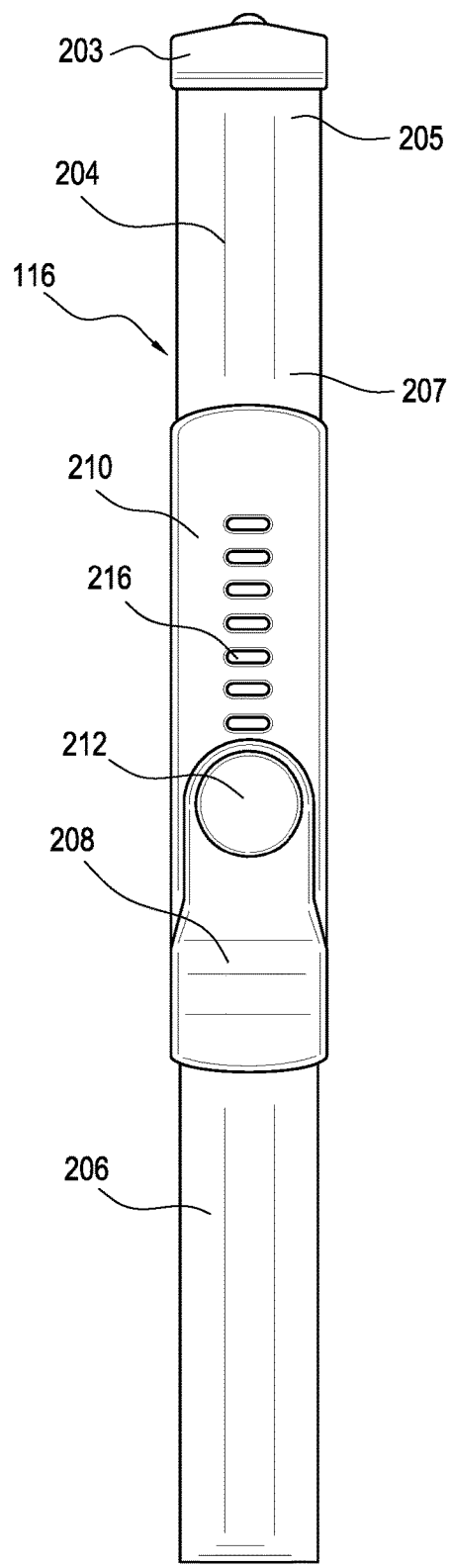
FIG. 12A is a plan view of an outer side of a third strap embodiment in the orthopedic device of FIG. 1.
Figure 12B:
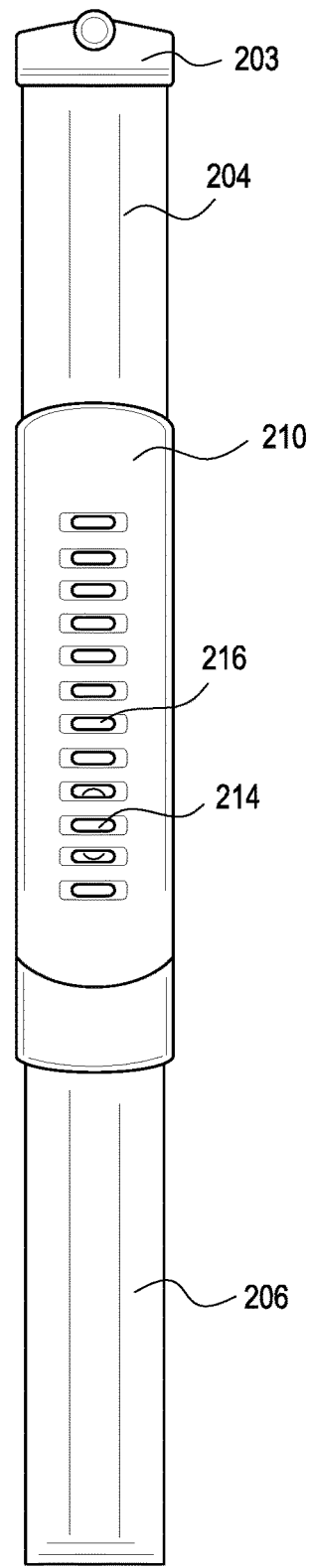
FIG. 12B is a plan view of an inner side of the third strap embodiment of FIG. 13A.
Figure 12C:
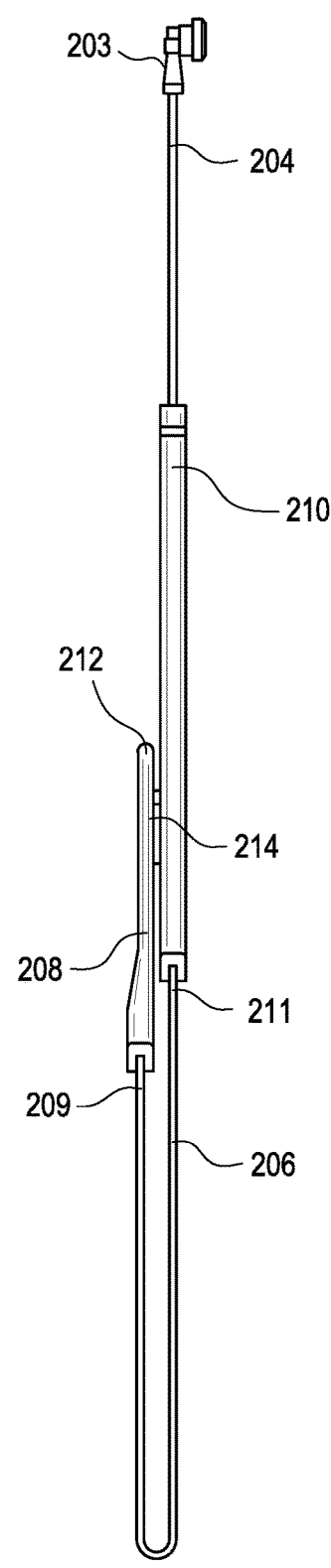
FIG. 12C is an elevational view of the third strap embodiment of FIG. 13A.

FIGS. 12A-12C depict an embodiment of the third strap 116 in connection with FIG. 2. Specifically, the strap 116 comprises a first strap segment 204 having first and second ends 205, 207, a second strap segment 206 having first and second ends 209, 211, a buckle 208 secured the first end 209 of the second strap segment 206. The buckle 208 carries a pin 214, and a band 210 secured to the second end 207 of the first strap segment 204. The second end 211 of the second strap segment 206, the band 210 forms apertures 216 arranged for securely and removably receiving the pin 214. The buckle 208 includes a head 212 extending beyond the first end 209 of the second strap segment 206, and the head 212 carries the pin 214. The second strap segment 206 forms a loop 218 between the first and second ends 209, 211, and is particularly adapted to extend about the bar 162 formed by the second shell 104. An anchoring bracket 203, which may be similar to the anchoring bracket 176, may be secured to the first strap end 205 in a manner similar to the embodiment of FIG. 11A.

The first and second strap segments 204, 206 are preferably formed from a textile such as having a construction comprising a loop laminate with a nylon webbing in the center core, similar to the elongate strap 174. The band 210 is preferably formed by a polymeric material but likely non-stretchable although flexible to bending. The buckle 208 may be formed similarly to the band 210. The pin 214 is preferably a rigid plastic material arranged for repeated securement or removal.

FIG. 12D illustrates how the third strap 116 extends over the second shell 104. The third strap 116 loops or extends about the bar 162. The third strap 116 is intended to extend over the calf antimigration portion 149 in order for the second shell 104 to provide additional reinforcement at such location when extending over the leg of the user. The anchoring bracket 176 will secure to the second keyhole 140, shown in FIG. 2, such that the third strap 116 is tensioned between the second keyhole 140 and the bar 162 when the buckle 208 secures to the band 210 by the pin 214 engaging the band 210 at one of the apertures 216. FIG. 12D exemplifies how the buckle 208 and the band 210 may include attachment portions 215, 217 that enable the buckle 208 and the band 210 to be molded and interlock to the first and second strap segments 204, 206.

FIGS. 13A and 13B exemplify a strap assembly embodiment 221 including a tightening mechanism 222 for adjusting at least one strap segment 228, 230 relative thereto. First and second molded segments 224, 226 connect the tightening mechanism 222 to first and second strap segments 228, 230. The molded segments 224, 226 may be elastic or inelastic, however they are preferably formed from a polymeric material. The molded segments 224, 226 have attachment portions 232, 234 that are molded over and integrally secured to the strap segments 228, 230 such that molded segments 224, 226 may be molded over the strap segments 228, 230. The attachment portions 232, 234, as in preceding embodiments, preferably secure above the strap segments 228, 230, which may be formed from a textile in that the material of the attachment portions 232, 234 mixes or spreads to interlock with fibers of the textile of the strap segments 228, 230.

The tightening mechanism 222 includes a base 238 upon which a dial 223 of the tightening mechanism 222 rotates to wind or unwind a cable 236 engaging the first molded segment 224. A sleeve 240 shrouds or encloses at least part of the molded segment 224, in that the first molded segment 224 carries a marker or indicia 242 that is present within a window 244 of the sleeve 240 to enable an understanding of tightening of the strap assembly 221. A part of the first molded segment 224 extends and slides over a portion 254 of the base 238, and the base 238 may be similarly flexible as the molded segments 224, 226 to enable the strap assembly 221 to yield to a shape of a user's body.

The cable 236 extends through grooves 246 defined by protrusions 248 formed by the first molded segment 224 such that when the sleeve 240 extends over the first molded segment 224, a loop of the cable 236 extends above the protrusions 248 and securely holds first molded segment 224 relative to the tightening mechanism 222. The base 238 forms guides 252 that likewise direct the cable 236 for winding and unwinding by the tightening mechanism 222, and therefore moving the first molded segment 224 and the accompanying first strap segment 228 relative to the tightening mechanism 222. The base 238 may be integrally secured to the second molded segment 226 by interlocking holes 256 formed by the base 238, and through which material of the second molded segment 226 may extend. The molded segment 226 may be adhered to the base 238.

The reinforcement edging and elements may be a film that is laminated over the sleeve 240 or pocket material, or other suitable materials may be employed. Suitable padding may be incorporated into the sleeve, although not shown in the drawings. Along an inside portion of the pockets or along the sleeve material, either the exterior surface or interior surface, pads may be provided that particularly correspond to the shape of the shells. In another variation, the pocket material may be formed by spacer material that has compressive and padding properties, and may be along one side of the pocket or both sides of the pocket so the shells are enclosed by the spacer material to provide padding to the user. The spacer material may have less stretchability and elasticity of the sleeve material to provide reinforcement to the area of the sleeve 240 at which the shells are located.

The orthopedic device has improved comfort characteristics due to the absence of features on the interior side of the shells, the overmolded edges of the shells, and the smooth inner surface of the sleeve. In addition, the padding that may be present at the pockets of the sleeve may better distribute pressure exerted on the leg of the user when the straps are tightened.

It is to be understood that not necessarily all objects or advantages may be achieved under any embodiment of the disclosure. For example, those skilled in the art will recognize that the orthopedic device may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct an orthopedic device in accordance with principles of the present disclosure. Additionally, it will be understood by the skilled artisan that the features described herein may be adapted to other types of orthopedic devices. Hence this disclosure and the embodiments and variations thereof are not limited to knee braces, but can be utilized in any orthopedic devices.

Although this disclosure describes certain exemplary embodiments and examples of an orthopedic device, it therefore will be understood by those skilled in the art that the present disclosure extends beyond the specifically disclosed knee brace embodiments to other alternative embodiments and/or uses of the disclosure and obvious modifications and equivalents thereof. Thus, it is intended that the scope of the present disclosure should not be limited by the particular disclosed embodiments described above, and may be extended to orthopedic devices and supports, and other applications that may employ the features described herein.

The invention claimed is:

1. A strap system having an adjustable length, the strap system comprising:
an elongate strap having a fixed length L1 and formed from a textile including a brushed loop material, and the elongate strap defining first and second ends;
a length adjustment system connected to the first end of the elongate strap, the length adjustment system including a belt segment having a first end secured to the first end of the elongate strap and defining a plurality of openings arranged along a portion of a length of the belt segment to a second end thereof, the belt segment being formed from a stretchable plastic material and substantially elastic along a length L2 of the belt segment;
a bracket selectively engageable with different openings among the plurality of openings to adjust the length L2 of the length adjustment system, wherein the bracket defines a fastener engageable to at least one opening among the plurality of openings;
wherein the belt segment has a first end of the belt segment defines defining a belt segment attachment portion, the belt segment attachment portion forms an overmold connection consisting of mixture or melding of the stretchable plastic material forming the belt segment attachment portion with the textile of the elongate strap, the belt segment integrally secured to and closed tightly around the first end of the elongate strap;
wherein the overmold connection forms part of the adjustable length of the strap system.

2. The strap system of claim 1, wherein the belt segment is trimmable from the second end thereof, thereby enabling a reduction in the plurality of openings.

3. The strap system of claim 1, wherein the belt segment defines at least one elongate slot defined between the first end and the plurality of openings.

4. The strap system of claim 3, wherein the at least one elongate slot extends completely through the belt segment.

5. The strap system of claim 1, wherein the fastener is defined by an extension portion generally having a length corresponding to a thickness of the belt segment, and a flange portion extending from the extension portion for securing against a surface of the belt segment.

6. The strap system of claim 1, wherein the belt segment defines a plurality of lateral recesses defined between the plurality of openings.

7. The strap system of claim 6, wherein the lateral recesses are defined along and in opposed pairs along inner and outer surfaces of the belt segment.

8. The strap system of claim 1, wherein each of said openings of the plurality of openings forming a keyhole shape for receiving a fastener of the bracket.

9. The strap system of claim 8, wherein the keyhole shape defines an insertion portion and a locking portion located in a direction of the second end of the belt segment opposite of the elongate strap.

10. The strap system of claim 9, wherein a seat portion is defined about the locking portion, and is formed by a recess sized and configured for receiving a flange portion of the bracket;
wherein the seat portion comprises an individual insert over which the belt segment is molded, the individual insert having a toughness greater than the belt segment.

11. The strap system of claim 1, wherein a mounting bracket is secured to a second end of the elongate strap.

12. The strap system of claim 1, wherein the belt segment defines a transition portion proximate the first end thereof and adjacent the belt segment attachment portion, the transition portion being formed as a reduced width and thickness portion extending to the second end of the belt segment.

13. The strap system of claim 12, wherein the belt segment attachment portion is wider than portions of the belt segment outside of the belt segment attachment portion extending toward the second end of the belt segment to accommodate a width of the elongate strap which is wider than said portions of the belt segment outside of the belt segment attachment portion;
wherein the transition portion defines a plurality of holes.

14. The strap system of claim 12, wherein the reduced thickness portion is thinner than the belt segment attachment portion.

15. The strap system of claim 1, wherein the belt segment defines at the first end a curved end.

16. The strap system of claim 1, wherein the bracket further comprises an anchoring bracket having an anchoring pin configured to selectively anchor the strap system to a separate component.

17. The strap system of claim 1, wherein the bracket defines a transition portion defined as a tapering between the fastener and an opposite end thereof.

18. The strap system of claim 1, wherein a portion of a length of the belt segment is molded over a reinforcing substrate with greater toughness than the belt segment.

19. A strap system having an adjustable length, the strap system comprising:
   an elongate strap having a fixed length L1 and formed from a textile including a brushed loop material, and the elongate strap defining first and second ends;
   a length adjustment system connected to the first end of the elongate strap, the length adjustment system including a belt segment having a first end secured to the first end of the elongate strap and defining at least two openings arranged along a portion of a length of the belt segment to a second end thereof, the belt segment being formed from a stretchable plastic material and substantially elastic along a length L2 of the belt segment;
   a bracket selectively engageable with different openings among the at least two openings to adjust the length L2 of the length adjustment system, the bracket including at least one fastener engageable with the belt segment via one of the at least two openings;
   wherein the belt segment has a first end of the belt segment defines defining a belt segment attachment portion, the belt segment attachment portion forms an overmold connection consisting of mixture or melding of the stretchable plastic material forming the attachment portion with the textile of the elongate strap, the belt segment integrally secured to and closed tightly around the first end of the elongate strap;
   wherein the overmold connection forms part of the adjustable length of the strap system;
   wherein the belt segment attachment portion is wider than portions of the belt segment outside of the belt segment attachment portion extending toward the second end of the belt segment to accommodate a width of the elongate strap which is wider than said portions of the belt segment outside of the belt segment attachment portion.

* * * * *